(12) United States Patent
Lee et al.

(10) Patent No.: US 9,404,150 B2
(45) Date of Patent: Aug. 2, 2016

(54) METHODS AND COMPOSITIONS FOR UNIVERSAL SIZE-SPECIFIC PCR

(75) Inventors: Min Seob Lee, San Diego, CA (US); Yanfeng Yang, Dublin, CA (US)

(73) Assignee: SEQUENOM, INC., San Diego, CA (US)

( * ) Notice: Subject to any disclaimer, the term of this patent is extended or adjusted under 35 U.S.C. 154(b) by 1439 days.

(21) Appl. No.: 12/674,403

(22) PCT Filed: Aug. 28, 2008

(86) PCT No.: PCT/US2008/074692
§ 371 (c)(1),
(2), (4) Date: Jun. 6, 2011

(87) PCT Pub. No.: WO2009/032781
PCT Pub. Date: Mar. 12, 2009

(65) Prior Publication Data
US 2011/0294699 A1 Dec. 1, 2011

Related U.S. Application Data

(60) Provisional application No. 60/968,878, filed on Aug. 29, 2007.

(51) Int. Cl.
*C12Q 1/68* (2006.01)
(52) U.S. Cl.
CPC .............. *C12Q 1/686* (2013.01); *C12Q 1/6848* (2013.01)
(58) Field of Classification Search
None
See application file for complete search history.

(56) References Cited

U.S. PATENT DOCUMENTS

| 577,258 | A | 2/1897 | Innes |
|---|---|---|---|
| 4,656,127 | A | 4/1987 | Mundy |
| 4,683,195 | A | 7/1987 | Mullis et al. |
| 4,683,202 | A | 7/1987 | Mullis |
| 4,851,331 | A | 7/1989 | Vary et al. |
| 4,965,188 | A | 10/1990 | Mullis et al. |
| 5,075,212 | A | 12/1991 | Rotbart |
| 5,174,962 | A | 12/1992 | Brennan |
| 5,210,015 | A | 5/1993 | Gelfand et al. |
| 5,338,671 | A | 8/1994 | Scalice et al. |
| 5,360,819 | A | 11/1994 | Giese |
| 5,387,505 | A | 2/1995 | Wu |
| 5,419,966 | A | 5/1995 | Reed |
| 5,487,972 | A | 1/1996 | Gelfand et al. |

(Continued)

FOREIGN PATENT DOCUMENTS

| CN | 1610758 A | 4/2005 |
|---|---|---|
| WO | WO 97/37041 | 10/1997 |

(Continued)

OTHER PUBLICATIONS

Guo et al. (2006) Gene 381 pp. 18-23.*

(Continued)

*Primary Examiner* — Suchira Pande
(74) *Attorney, Agent, or Firm* — Grant IP, Inc.

(57) ABSTRACT

Provided herein are products and processes for the amplification, detection and sequencing of short-stranded nucleic acid in the presence of a high background of long-stranded genomic material (e.g., host or maternal nucleic acids). The methods rely on the use of inside and outside primers introduced at varying concentrations, as well as universal amplification reactions that preferentially amplify short, low copy number nucleic acid.

34 Claims, 8 Drawing Sheets

(56) References Cited

U.S. PATENT DOCUMENTS

| | | |
|---|---|---|
| 5,492,806 A | 2/1996 | Drmanac et al. |
| 5,512,677 A | 4/1996 | Chern |
| 5,516,931 A | 5/1996 | Giese |
| 5,525,464 A | 6/1996 | Drmanac et al. |
| 5,547,835 A | 8/1996 | Koster |
| 5,585,481 A | 12/1996 | Arnold |
| 5,587,287 A | 12/1996 | Scalice et al. |
| 5,589,330 A | 12/1996 | Shuber |
| 5,605,798 A | 2/1997 | Koster |
| 5,656,493 A | 8/1997 | Mullis et al. |
| 5,660,988 A | 8/1997 | Duck et al. |
| 5,665,539 A | 9/1997 | Sano |
| 5,677,152 A | 10/1997 | Birch et al. |
| 5,679,524 A | 10/1997 | Nikiforov et al. |
| 5,691,141 A | 11/1997 | Koster |
| 5,695,940 A | 12/1997 | Drmanac et al. |
| 5,696,251 A | 12/1997 | Arnold |
| 5,719,028 A | 2/1998 | Dahlberg |
| 5,736,626 A | 4/1998 | Mullah |
| 5,770,367 A | 6/1998 | Southern et al. |
| 5,786,146 A | 7/1998 | Herman et al. |
| 5,801,155 A | 9/1998 | Kutyavin et al. |
| 5,834,189 A | 11/1998 | Stevens et al. |
| 5,849,483 A | 12/1998 | Shuber |
| 5,849,542 A | 12/1998 | Reeve et al. |
| 5,851,770 A | 12/1998 | Babon et al. |
| 5,869,242 A | 2/1999 | Kamb |
| 5,876,934 A | 3/1999 | Duthie et al. |
| 5,891,625 A | 4/1999 | Buchardt et al. |
| 5,908,755 A | 6/1999 | Kumar et al. |
| 5,912,118 A | 6/1999 | Ansorge et al. |
| 5,928,906 A | 7/1999 | Koster et al. |
| 5,942,610 A | 8/1999 | Nelson |
| 5,952,174 A | 9/1999 | Nikiforov et al. |
| 5,958,692 A | 9/1999 | Cotton et al. |
| 5,976,802 A | 11/1999 | Ansorge et al. |
| 5,981,186 A | 11/1999 | Gabe et al. |
| 5,998,143 A | 12/1999 | Ellis et al. |
| 6,004,744 A | 12/1999 | Goelet et al. |
| 6,013,431 A | 1/2000 | Soderlund et al. |
| 6,013,499 A | 1/2000 | Narumiya et al. |
| 6,017,702 A | 1/2000 | Lee et al. |
| 6,018,041 A | 1/2000 | Drmanac et al. |
| 6,043,031 A | 3/2000 | Koster et al. |
| 6,045,996 A | 4/2000 | Cronin et al. |
| 6,046,005 A | 4/2000 | Ju et al. |
| 6,087,095 A | 7/2000 | Rosenthal et al. |
| 6,110,684 A | 8/2000 | Kemper et al. |
| 6,127,121 A | 10/2000 | Meyer, Jr. et al. |
| 6,136,541 A | 10/2000 | Gulati |
| 6,140,054 A | 10/2000 | Wittwer et al. |
| 6,142,681 A | 11/2000 | Gulati |
| 6,156,501 A | 12/2000 | McGall et al. |
| 6,183,958 B1 | 2/2001 | Stanton, Jr. |
| 6,190,865 B1 | 2/2001 | Jendrisak et al. |
| 6,194,144 B1 | 2/2001 | Koster |
| 6,197,506 B1 | 3/2001 | Fodor et al. |
| 6,210,891 B1 | 4/2001 | Nyren et al. |
| 6,214,560 B1 | 4/2001 | Yguerabide et al. |
| 6,223,127 B1 | 4/2001 | Berno |
| 6,225,625 B1 | 5/2001 | Pirrung et al. |
| 6,229,911 B1 | 5/2001 | Balaban et al. |
| 6,239,273 B1 | 5/2001 | Pease et al. |
| 6,251,639 B1 | 6/2001 | Kurn |
| 6,258,538 B1 | 7/2001 | Koster et al. |
| 6,258,540 B1 | 7/2001 | Lo et al. |
| 6,261,768 B1 | 7/2001 | Todd et al. |
| 6,268,129 B1 | 7/2001 | Gut |
| 6,312,894 B1 | 11/2001 | Hedgpeth et al. |
| 6,322,980 B1 | 11/2001 | Singh |
| 6,426,408 B1 | 7/2002 | Kutyavin et al. |
| 6,436,640 B1 | 8/2002 | Simmons et al. |
| 6,511,809 B2 | 1/2003 | Baez |
| 6,514,700 B1 | 2/2003 | Singh |
| 6,613,509 B1 | 9/2003 | Chen |
| 6,635,452 B1 | 10/2003 | Monforte |
| 6,649,351 B2 | 11/2003 | Matray |
| 6,723,513 B2 | 4/2004 | Lexow |
| 6,762,298 B2 | 7/2004 | Beaucage et al. |
| 6,797,470 B2 | 9/2004 | Barany |
| 6,812,005 B2 | 11/2004 | Fan |
| 6,878,515 B1 | 4/2005 | Landegren |
| 6,890,741 B2 | 5/2005 | Fan |
| 6,927,028 B2 | 8/2005 | Dennis et al. |
| 7,169,314 B2 | 1/2007 | Unger et al. |
| 7,172,861 B2 | 2/2007 | Keener et al. |
| 7,244,567 B2 | 7/2007 | Chen et al. |
| 7,252,940 B2 | 8/2007 | Kutyavin et al. |
| 7,255,992 B2 | 8/2007 | Ecker |
| 7,745,136 B1 | 6/2010 | Dorsey |
| 7,781,162 B2 | 8/2010 | Ecker |
| 7,902,345 B2 | 3/2011 | Van Den Boom |
| 8,133,701 B2 | 3/2012 | Van Den Boom |
| 8,383,795 B2 | 2/2013 | Van Den Boom |
| 2001/0031467 A1 | 10/2001 | Dapprich |
| 2002/0006617 A1 | 1/2002 | Fan |
| 2002/0022224 A1 | 2/2002 | Hornby |
| 2002/0064779 A1 | 5/2002 | Landegren |
| 2003/0027135 A1 | 2/2003 | Ecker et al. |
| 2003/0036064 A1 | 2/2003 | Stuelpnagel |
| 2003/0049657 A1 | 3/2003 | Cherry |
| 2003/0082539 A1 | 5/2003 | Ecker et al. |
| 2003/0082600 A1 | 5/2003 | Olek et al. |
| 2003/0104434 A1 | 6/2003 | Fan |
| 2003/0108900 A1 | 6/2003 | Oliphant |
| 2003/0124556 A1 | 7/2003 | Ecker et al. |
| 2003/0170684 A1 | 9/2003 | Fan |
| 2003/0175695 A1 | 9/2003 | Ecker et al. |
| 2003/0175696 A1 | 9/2003 | Ecker et al. |
| 2003/0175697 A1 | 9/2003 | Ecker et al. |
| 2003/0180779 A1 | 9/2003 | Lofton-Day et al. |
| 2003/0190605 A1 | 10/2003 | Ecker |
| 2003/0194717 A1 | 10/2003 | Schmidt |
| 2003/0211489 A1 | 11/2003 | Shen et al. |
| 2003/0211522 A1 | 11/2003 | Landes et al. |
| 2004/0101893 A1 | 5/2004 | Kutyavin et al. |
| 2004/0121364 A1 | 6/2004 | Chee |
| 2004/0137470 A1 | 7/2004 | Dhallan |
| 2004/0203037 A1 | 10/2004 | Lo |
| 2004/0224352 A1 | 11/2004 | Fan |
| 2005/0016424 A1 | 1/2005 | Ellington |
| 2005/0037388 A1 | 2/2005 | Antonarakis et al. |
| 2005/0053939 A1 | 3/2005 | Chenna et al. |
| 2005/0112590 A1 | 5/2005 | Boom et al. |
| 2005/0233351 A1 | 10/2005 | Landegren |
| 2005/0239068 A1 | 10/2005 | Bosnes |
| 2005/0287533 A1 | 12/2005 | Ehrich et al. |
| 2005/0287592 A1 | 12/2005 | Kless |
| 2006/0019278 A1 | 1/2006 | Lo et al. |
| 2006/0024695 A1 | 2/2006 | Li |
| 2006/0040304 A1 | 2/2006 | Blumenfeld et al. |
| 2006/0057596 A1 | 3/2006 | Keener et al. |
| 2006/0094039 A1 | 5/2006 | Rosenfeld et al. |
| 2006/0160105 A1 | 7/2006 | Dhallan |
| 2006/0166249 A1 | 7/2006 | Rothberg et al. |
| 2006/0172319 A1 | 8/2006 | Yan |
| 2006/0234252 A1 | 10/2006 | Anderson |
| 2006/0252068 A1 | 11/2006 | Lo et al. |
| 2006/0252071 A1 | 11/2006 | Lo et al. |
| 2007/0059707 A1 | 3/2007 | Cantor et al. |
| 2007/0202525 A1 | 8/2007 | Quake et al. |
| 2007/0219361 A1 | 9/2007 | Bodepudi et al. |
| 2008/0050725 A1 | 2/2008 | Keener |
| 2008/0096766 A1* | 4/2008 | Lee .................... 506/6 |
| 2008/0305479 A1 | 12/2008 | Van Den Boom |
| 2009/0202984 A1 | 8/2009 | Cantor |
| 2010/0159447 A1 | 6/2010 | Li et al. |
| 2011/0160093 A1 | 6/2011 | Van Den Boom |
| 2014/0235464 A1 | 8/2014 | Van Den Boom et al. |

FOREIGN PATENT DOCUMENTS

| | | |
|---|---|---|
| WO | WO 00/52625 | 9/2000 |
| WO | WO 01/20039 | 3/2001 |

(56) References Cited

FOREIGN PATENT DOCUMENTS

| | | |
|---|---|---|
| WO | WO 01/25485 | 4/2001 |
| WO | WO 01/27326 | 4/2001 |
| WO | WO 01/27329 | 4/2001 |
| WO | WO 01/29259 | 4/2001 |
| WO | WO 2006/056480 | 5/2002 |
| WO | WO 2004/007755 | 1/2004 |
| WO | WO 2004/018626 | 3/2004 |
| WO | WO 2005/023091 | 3/2005 |
| WO | WO 2005/090599 | 9/2005 |
| WO | WO 2005/098042 | 10/2005 |
| WO | WO 2005/113804 | 12/2005 |
| WO | WO 2006/056478 | 6/2006 |
| WO | WO 2007/060707 | 5/2007 |
| WO | WO 2007/069991 | 6/2007 |
| WO | WO 2007/071232 | 6/2007 |
| WO | WO 2007/111937 | 10/2007 |
| WO | WO 2007/140417 | 12/2007 |
| WO | WO 2007/147063 | 12/2007 |
| WO | WO 2008/118988 | 9/2008 |
| WO | WO 2008/136868 | 11/2008 |
| WO | WO 2009/032779 | 3/2009 |
| WO | WO 2009/032781 | 3/2009 |
| WO | WO 2009/073251 | 6/2009 |
| WO | WO 2010/107946 | 9/2010 |

OTHER PUBLICATIONS

Li et al. (2006) Clinical chemistry vol. 52: 4 pp. 624-633.*
Nazarenko et al. (2002) Nucleic Acid Research vol. 30 No. 9 e37 newly cited.*
Office Action mailed on Aug. 30, 2013 in U.S. Appl. No. 12/726,246, filed Mar. 17, 2010 and published as US 2010/0279295 on Nov. 4, 2010.
Office Action mailed on Oct. 21, 2013 in U.S. Appl. No. 12/726,246, filed Mar. 17, 2010 and published as US 2010/0279295 on Nov. 4, 2010.
Amicucci et al.., (2000) Clin Chem 46:301-302.
Anker and Stron, Clin Chem (2002) 48, 1210-1211.
Anker et al., Cancer Metastasis rev (1999) 18;65-73.
Archer et al., Anal Biocham 15:355(2):285-297 Aug. 15, 2006.
Brown et al., Methods Enzymol 68:109-151(1979).
Chan and Lo, Histol Histopathol (2002) 17;937-943.
Chan et al., Clin Chem Jan. 2004;50(1);88-92.
Chen et al., Nat Med 1996:2:1033-1035.
Chiu et al., (2002) Lancet 360:998-1000.
Costa et al, Prenat Diagn 21:1070-1074.
Costa et al., (2002) Clin Chem 48:(679-680.
Extended European Search Report mailed on Oct. 10, 2010, in European Application No. 08798915 filed on Aug. 28, 2008.
Finning et al., (2002) Transfusion 42:1079-1085.
Fournie et al., Cancer Lett 1995:91-221-227.
Fournie et al., Gerontology 1993:39:215-221.
Fucharoen et al, (2003) Prenat Diagn 23:393-396.
Gonzolez-Gonzolez MC, et al., (2003) Prenat Diagn 23:232-234.
Green et al., Nucleic Acids Research 18:6163-6164 (1990).
Grompe et al., Nature Genetics 5:111-117 (1993).
Grompe et al., PNAS USA 86:5855-5892 (1989).
Bischoff et al., Human Reprod Update Jan.-Feb. 2005;11(1):59-67.
International Search Report and Written Opinion mailed on: Mar. 27, 2009 in International Application No. PCT/US2008/074692 filed on: and published as: WO 09/032781 on Mar. 12, 2009.
International Preliminary Report on Patentability mailed on: Mar. 3, 2010 in International Application No. PCT/US2008/074692 filed on: and published as: WO 09/032781 on Mar. 12, 2009.
Jahr et al., Cancer Res (2001) 61;1659-1665.
Kandpal et al., Nucleic Acids Research 18:1789-1795 (1990).
Kaneoka et al., Biotechniques 10:30-34 (1991).
Li et al., Clin Chem. Jun. 2004;50(6):1002-1011.
Lo et al, (1998) N Engl J Med 339:1734-1738.
Lo et al., Am J Hum Genet (1998) 62:768-775.
Lo et al., Am J Hum Genet (1999) 64:218-224.
Lo et al., Clin Chem (1999) 45,1292-1294.
Lo et al., Clin Chem 2000;46:319-323.
Lo et al., Lancet 1998;351:1329-1230.
Narang et al., Methods Enzymol 68:9-98 (1979).
Nawroz et al., Nat Med 1996:2:1035-1037.
Ng et al., PNAS USA (2003) 100;4748-4753.
Orita et al. PNAS USA (1989) 86:27776-27770.
Protocols: A Guide to Methods and Applications, Innis et al., eds 1990.
Rijnders et al., (2001) Obstet Gynecol 98:374-378.
Rumore and Steinman, J Clin Invest Jul. 1990;86(1):69-74.
Saiki et al., Science 239:487, 1998.
Saito et al., (2000) Lancet 356:1170.
Sheffield et al. PNAS USA 49:699-706 (1991).
Streptawell, transparent, High-Bind plates from: Roche Molecular Biochemicals, Cataloge No. 1-645-692 as listed in Biochemicals Catalog (2001).
Stroun et al., Oncology (1989) 46;318-322.
White et al., Genomics 12:301-306 (1992).
Alseth et al., "A general role of the DNA glycosylase Nth1 in the abasic sites cleavage step of base excision repair in Schizosaccharomyces pombe," Nucleic Acids Research, 2004, vol. 32, No. 17 5119-5125.
Amicucci et al., (2000) Clin Chem 46:301-302.
Anantha et al., "Porphyrin binding to quadrupled T4G4." Biochemistry. Mar. 3, 1998;37(9):2709-14.
Braslaysky et al., "Sequence information can be obtained from single DNA molecules." Proc Natl Acad Sci U S A. Apr. 1, 2003;100(7):3960-4.
Brent et al., "Using protein-DNA chimeras to detect and count small numbers of molecules", Nat Methods. Jan. 2005;2(1):31-37.
Brown et al., (Chemical synthesis and cloning of a tyrosine tRNA gene, Methods Enzymol 68:190-151 (1979).
Bruenner et al., "Quantitative analysis of oligonucleotides by matrix-assisted laser desorption/ionization mass spectrometry." Rapid Commun Mass Spectrom. 1996;10(14):1797-801.
Burlingame et al. "Mass spectrometry," Anal. Chem. 70:647R-716R (1998).
Chen et al., "Fluorescence energy transfer detection as a homogeneous DNA diagnostic method." Proc Natl Acad Sci U S A. Sep. 30, 1997;94(20):10756-10761.
Chen X, Kwok Py., "Template-directed dye-terminator incorporation (TDI) assay: a homogeneous DNA diagnostic method based on fluorescence resonance energy transfer." Nucleic Acids Res. Jan. 15, 1997;25(2):347-53.
Costa et al., (2002) Clin Chem 48:(679-680).
Current Protocols in Molecular Biology, John Wiley & Sons, N.Y., 6.3.1-6.3.6 (1989).
Davis et al., "A knockin mouse model of the Bardet-Biedl syndrome 1 M390R mutation has cilia defects, ventriculomegaly, retinopathy, and obesity." Proc Natl Acad Sci U S A. Dec. 4, 2007;104(49):19422-7.
Dear Ph., "One by one: Single molecule tools for genomics." Brief Funct Genomic Proteomic. Jan. 2003;1(4):397-416.
Ding and Cantor, "A high-throughput gene expression analysis technique using competitive PCR and matrix-assisted laser desorption ionization time-of-flight MS," Proc Natl Acad Sci U S A. Mar. 18, 2003;100(6):3059-3064.
Egger et al., "Reverse transcription multiplex PCR for differentiation between polio- and enteroviruses from clinical and environmental samples." J Clin Microbiol. Jun. 1995;33(6)1442-7.
Grompe et al., "Scanning detection of mutations in human ornithine transcarbamoylase by chemical mismatch cleavage." Proc Natl Acad Sci U S A. Aug. 1989;86(15):5888-92.
Grompe M., "The rapid detection of unknown mutations in nucleic acids." Nat Genet. Oct. 1993;5(2):111-117.
Haase et al., Methods in Virology, pp. 189-226, 1984.
Haff, "Multiplex Genotyping of PCR Products with Mass Tag-Labled Primers," Nucleic Acids Res. (1997) vol. 25, No. 18, pp. 3749-3750.
Hames and Higgins eds., Nucleic Acid Hybridization: A Practical Approach, IRL Press, 1985.

(56) References Cited

OTHER PUBLICATIONS

Harris et al., "Single-molecule DNA sequencing of a viral genome." Science. Apr. 4, 2008;320(5872)106-9.
Heid et al., "Real time quantitative PCR," Genome Methods 6:986-994, 1996.
Hill, Craig, "Gen-Probe Transcription-Mediated Amplification: System Principles," Jan. 1996 httl://www.gen-probe.com/pdfs/tma_whiteppr.pdf.
Innis et al., PCR Protocols: A Guide to Methods and Applications, eds, 1990.
Isola et al., "Matrix-assisted laser desorption/ionization detection of polymerase chain reaction products by utilizing the 5'-3' exonuclease activity of Thermus aquaticus DNA polymerase," Rapid Communications in Mass Spectrometry, vol. 17, No. 6, 2003, pp. 532-537.
Jurinke et al., "MALDI-TOF mass spectrometry: a versatile tool for high-performance DNA analysis." Mol Biotechnol. Feb. 2004;26(2):147-64.
Jurinke et al., "The use of MassARRAY technology for high throughput genotyping," Adv Biochem Eng Biotechnol (2002) 77:57-74.
Kaiser et al., "A comparison of eubacterial and archaeal structure-specific 5'-exonucleases." J. Biol. Chem. 274:21387-21394 (1999).
Kalinina et al., "Nanoliter scale PCR with TaqMan detection." Nucleic Acids Res. May 15, 1997;25(10):1999-2004.
Kinter and Sherman, Protein Sequencing and Identification Using Tandem Mass Spectrometry Wiley-Interscience, New York (2000).
Kokoska et al., "Low fidelity DNA synthesis by a Y family DNA polymerase due to misalignment in the active site," Journal of Chemistry, vol. 277, No. 22, pp. 19633-19638, 2002.
Lesiak et al., "2',5'-Oligoadenylate:antisense chimeras—synthesis and properties." Bioconjug Chem. Nov.-Dec. 1993;4(6):467-72.
Lo et al., N Eng J Med 1998:339:1734-1738.
Lo Ym., "Recent advances in fetal nucleic acids in maternal plasma." J Histochem Cytochem. Mar. 2005;53(3):293-6.
Lyamichev et al., "Comparison of the 5' nuclease activities of taq DNA polymerase and its isolated nuclease domain," Proc. Natl. Acad. Sci. USA 96:6143-6148 (1999).
Ma et al., "RNA template-dependent 5' nuclease activity of Thermus aquaticus and *Thermus thermophilus* DNA polymerases," J. Biol. Chem. 275:24693-24700 (2000).
Margulies et al., "Genome sequencing in microfabricated high-density picolitre reactors." Nature. Sep. 15, 2005;437(7057):376-80.
Nakano et al., "Single-molecule PCR using water-in-oil emulsion." J Biotechnol. Apr. 24, 2003;102(2):117-24.
Narang et al., Methods Enzymol 68:90 (1979).
Needham-VanDevanter et al., "Characterization of an adduct between CC-1065 and a defined oligodeoxynucleotide duplex." Nucleic Acids Res. Aug. 10, 1984;12(15):6159-68.
Niemeyer, C. M. et al., "Immuno-PCR: high sensitivity detection of proteins by nucleic acid amplification", Trends in Biotechnology, 2005, 23 (4), 208-216.
Nolte Fs., "Branched DNA signal amplification for direct quantitation of nucleic acid sequences in clinical specimens." Adv Clin Chem. 1998;33:201-35.
Oeth, P. et al., "iPLEX™ Assay: Increased Flexing Efficiency and Flexibility for MassARRAY® System through single base primer extension with mass-modified Terminators." SEQUENOM Application Note (2005).
Orita et al., "Detection of polymorphisms of human DNA by gel electrophoresis as single-strand conformation polymorphisms." Proc Natl Acad Sci U S A. Apr. 1989;86(8):2766-2770.
Pearson and Regnier, J. Chrom., 255:137-149, 1983.
Qu X, Chaires Jb., "Analysis of drug-DNA binding data." Methods Enzymol. 2000;321:353-69.
Reddy, et al., "Synthetic DNA minor groove-binding drugs," Pharmacol. Therap. 84:1-111 (1999).
Romero and Rotbart in Diagnostic Molecular Biology: Principles and Applications pp. 401-406, Persing et al., eds., Mayo Foundation, Rochester, Minn., 1993.
Ross, "Discrimination of single-nucleotide polymorphisms in human DNA using peptide nucleic acid probes detected by MALDI-TOF mass spectrometry," Anal. Chem (1997) 69:4197-4202.
Sambrook and Russell, Molecular Cloning: A Laboratory Manual 3d ed., 2001.
Sheffield et al., "Identification of novel rhodopsin mutations associated with retinitis pigmentosa by GC-clamped denaturing gradient gel electrophoresis." Am J Hum Genet. Oct. 1991;49(4):699-706.
Singer et al., Biotechniques 4:230, 1986.
Soni Gv, Meller A., "Progress toward ultrafast DNA sequencing using solid-state nanopores." Clin Chem. Nov. 2007;53(11):1996-2001.
Streptawell, transparent, High-Bind plates from: Roche Molecular Biochemicals, Cataloge No. 1-645-692 as listed in Biochemicals Catalog (2004).
Venter et al., "The sequence of the human genome." Science. Feb. 16, 2001;291(5507):1304-51.
Verbeck et al., "A fundamental introduction to ion mobility mass spectrometry applied to the analysis of biomolecules," Journal of Biomolecular Techniques vol. 13, Issue 2, 56-61.
Vincent et al., "Helicase-dependent isothermal DNA amplification." EMBO Rep. Aug. 2004;5(8):795-800.
Vogelstein B, Kinzler Kw., "Digital PCR." Proc Natl Acad Sci U S A. Aug. 3, 1999;96(16):9236-41.
Walker, et al., "Progress in the design of DNA sequence-specific lexitropsins," Biopolymers 44:323-334 (1997).
Wemmer & Dervan, "Targeting the minor groove of DNA," Current Opinon in Structural Biology 7:355-361 (1997).
White et al., "Detecting single base substitutions as heteroduplex polymorphisms." Genomics. Feb. 1992;12(2):301-306.
White, "The future of PCR technology: diversification of technologies and applications," Trends in Biotechnology (1996) 14(12); 478-483.
Wilkinson, "In situ Hybridization, A Practical Approach," Wilkinson ed., IRL Press, Oxford University Press, Oxford (1998).
Zhang et al., "Location of abasic sites in oligodeoxynucleotides by tandem mass spectrometry and by a chemical clevage initiates by an unusual reaction of the ODN with MALDI matrix," Journal of the American Society for Mass Spectrometry, Elsevier Science Inc. US vol. 13, No. 12, Dec. 1, 2002, 1418-1426.
Zimmer & Wahnert, "Nonintercalating DNA-binding ligands: specificity of the interaction and their use as tools in biophysical, biochemical and biological investigations of the genetic material," Prog. Biophys. Molec. Bio. 47:31-112 (1986).
Extended European Search Report mailed on Sep. 21, 2010, in European Application No. EP0787342 filed on Dec. 4, 2007.
Extended European Search Report mailed on Oct. 1, 2010, in European Application No. 08798915 filed on Aug. 28, 2008.
Extended European Search Report mailed on Jan. 7, 2013, in European Application No. EP10754078 filed on Mar. 17, 2010.
International Preliminary Report on Patentability dated Jun. 18, 2009 in International Application No. PCT/US2007/86425 Filed, Dec. 4, 2007 and published as: WO/2008/136868 on Nov. 13, 2008.
International Search Report/Written dated Dec. 22, 2008 in International Application No. PCT/US2007/86425 Filed, Dec. 4, 2007 and published as: WO/2008/136868 on Nov. 13, 2008.
International Preliminary Report on Patentability dated: Jun. 17, 2010 in International Application No. PCT/US2008/065882 filed, Jun. 4, 2008 and published as WO/2009/073251 on Jun. 11, 2009.
International Search Report/Written dated: Dec. 19, 2008 in International Application No. PCT/US2008/065882 filed, Jun. 4, 2008 and published as WO/2009/073251 on Jun. 11, 2009.
International Preliminary Report on Patentability mailed on: Mar. 11, 2010 in International Application No. PCT/US2008/074692 filed on: Aug. 28, 2008 and published as: WO 09/032781 on Mar. 12, 2009.
International Search Report and Written Opinion mailed on: Mar. 27, 2009 in International Application No. PCT/US2008/074692 filed on: Aug. 28, 2008 and published as: WO 09/032781 on Mar. 12, 2009.
International Preliminary Report on Patentability mailed on: Sep. 29, 20110 in International Application No. PCT/US2010/027706 filed on: Mar. 17, 2010 and published as: WO 10/107946 on Sep. 23, 2010.

(56) References Cited

OTHER PUBLICATIONS

International Search Report and Written Opinon mailed on: Dec. 22, 2010 in International Application No. PCT/US2010/027706 filed on: Mar. 17, 2010 and published as: WO 10/107946 on Sep. 23, 2010.
Office Action dated: Oct. 24, 2012 in U.S. Appl. No. 13/040,056, filed Mar. 3, 2011, published as: US/2011/0160093 and Issued as: 8,383,795 on Feb. 26, 2013.
Office Action dated: Sep. 4, 2012 in U.S. Appl. No. 13/040,056, filed Mar. 3, 2011, published as: US/2011/0160093 and Issued as: 8,383,795 on Feb. 26, 2013.
Office Action dated: Feb. 14, 2012 in U.S. Appl. No. 13/040,056, filed Mar. 3, 2011, published as: US/2011/0160093 and Issued as: 8,383,795 on Feb. 26, 2013.
Office Action dated: Oct. 29, 2010 in U.S. Appl. No. 12/133,327, filed Jun. 4, 2008 3, 2011, published as: US/2009/0111712 on Apr. 30, 2009 and Issued as: 7,902,345 on Mar. 8, 2011.
Office Action dated: Mar. 11, 2010 in U.S. Appl. No. 12/133,327, filed Jun. 4, 2008 3, 2011, published as: US/2009/0111712 on Apr. 30, 2009 and Issued as: 7,902,345 on Mar. 8, 2011.
Office Action dated: Nov. 14, 2011 in U.S. Appl. No. 11/950,395, filed Dec. 4, 2007, published as: US/2008/0305479 on Dec. 11, 2008 and Issued as: 8,133,701 on Mar. 13, 2012.
Office Action dated: Apr. 26, 2011 in U.S. Appl. No. 11/950,395, filed Dec. 4, 2007, published as: US/2008/0305479 on Dec. 11, 2008 and Issued as: 8,133,701 on Mar. 13, 2012.
Office Action dated: Oct. 13, 2010 in U.S. Appl. No. 11/950,395, filed Dec. 4, 2007, published as: US/2008/0305479 on Dec. 11, 2008 and Issued as: 8,133,701 on Mar. 13, 2012.
Office Action dated: Mar. 2, 2010 in U.S. Appl. No. 11/950,395, filed Dec. 4, 2007, published as: US/2008/0305479 on Dec. 11, 2008 and Issued as: 8,133,701 on Mar. 13, 2012.
Office Action dated: May 8, 2013 in U.S. Appl. No. 12/726,246, filed Mar. 17, 2010, published as: US/2010/0279295 on Nov. 4, 2010.
Office Action dated: Sep. 13, 2012 U.S. Appl. No. 12/726,246, filed Mar. 17, 2010, published as: US/2010/0279295 on Nov. 4, 2010.
Office Action mailed on Dec. 9, 2014 in U.S. Appl. No. 12/726,246, filed Mar. 17, 2010 and published as US 2010/0279295 on Nov. 4, 2010.
Office Action mailed on May 29, 2014 in U.S. Appl. No. 12/726,246, filed Mar. 17, 2010 and published as US 2010/0279295 on Nov. 4, 2010.
Office Action mailed on Jul. 10, 2014 in U.S. Appl. No. 13/766,482, filed Feb. 13, 2013 and published as US 2014/0235464 on Aug. 21, 2014.
Oeth et al., "Gene Expression Analysis Using Competitive PCR and MassARRAY" Sequenom Application Note, Doc.No. 8876-002, ROO, CO 040123, Apr. 12, 2004.
Park et al., "Measuring Allele-Specific Expression Using MassARRAY" Sequenom Application Note, Doc.No. 8876-005, RO1, CO 040378, Sep. 17, 2004.
Beaulieu et al., Chapter 16 "MALDI-TOF MS: Applications in Genomics" in Pharmacogenomics, second edition, Kalow et al., eds. (2005), pp. 353-387.
Sequenom, "Multiplexing the Homogenous Mass Extend Assay" Sequenom Application Note, Doc No. 8876-001, R01, CO 040038, Jan. 28, 2004.
Poynton, "Writing SI units and symbols" Aug. 17, 2006, www.poynton.com.
Oeth et al., "Qualitative and quantitative genotyping using single base primer extension coupled with matrix-assisted laser desorption/ionization time-of-flight mass spectrometry (MassARRAY)" Methods Mol. Biol. (2009) 578:307-343.
Van Den Boom et al., "MALDI-TOF MS: a platform technology for genetic discovery" International Journal of Mass Spectrometry (2004) 238:173-188.
Andell et al., "Multiplexed Gene Expression Analysis Using Competitive PCR and MassARRAY" Sequenom Application Note, Doc. No. 8876-003, ROO, CO 040124, Mar. 31, 2004.
Oeth et al., "iPLEX Assay: Increased Plexing Efficiency and Flexibility for MassARRAY System Through Single Base Primer Extension With Mass-Modified Terminators" Sequenom Application Note, Doc.No. 8876-006, RO4, CO 060150, Nov. 10, 2006.

* cited by examiner

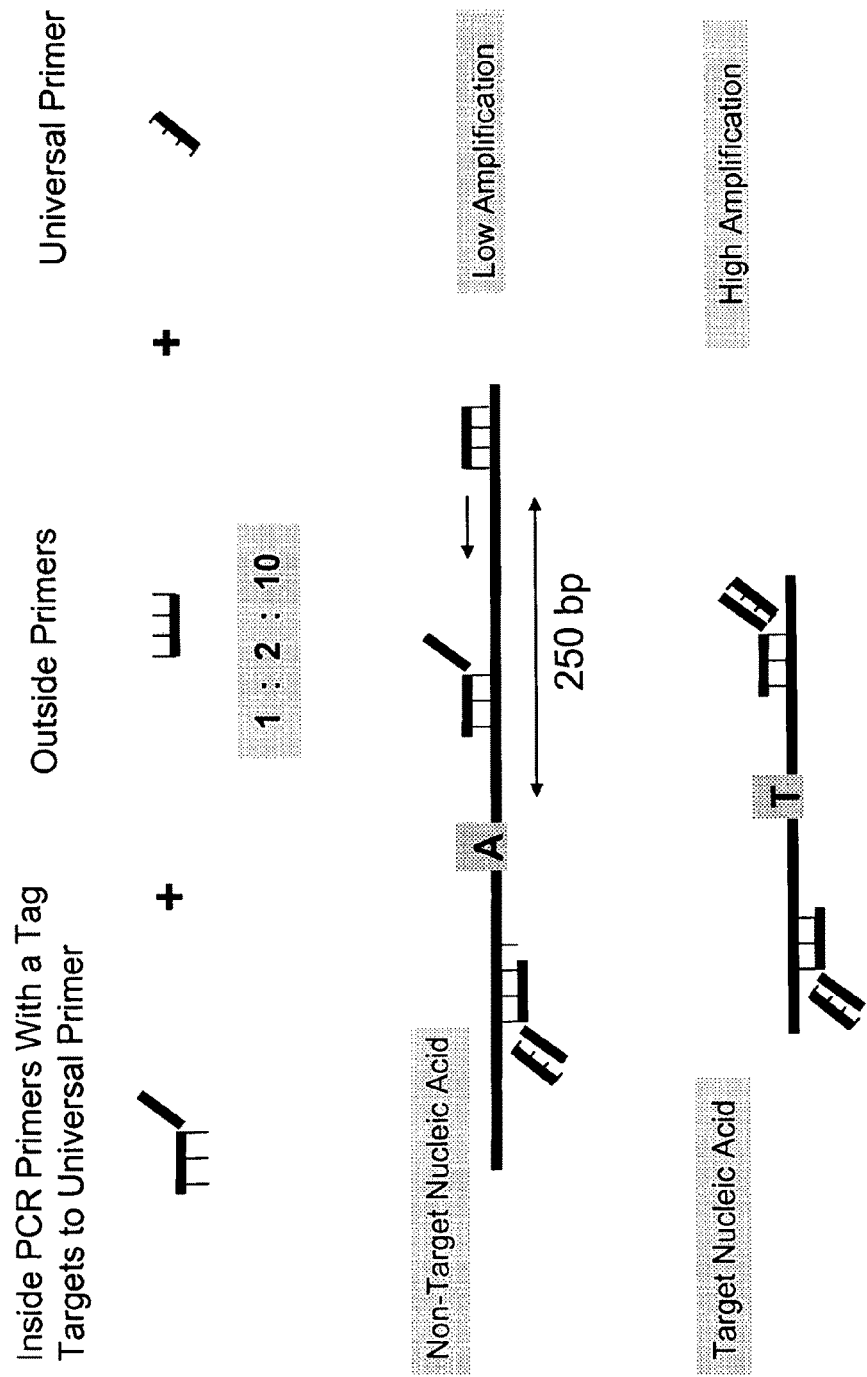

Universal Sequence Specific (USES) PCR

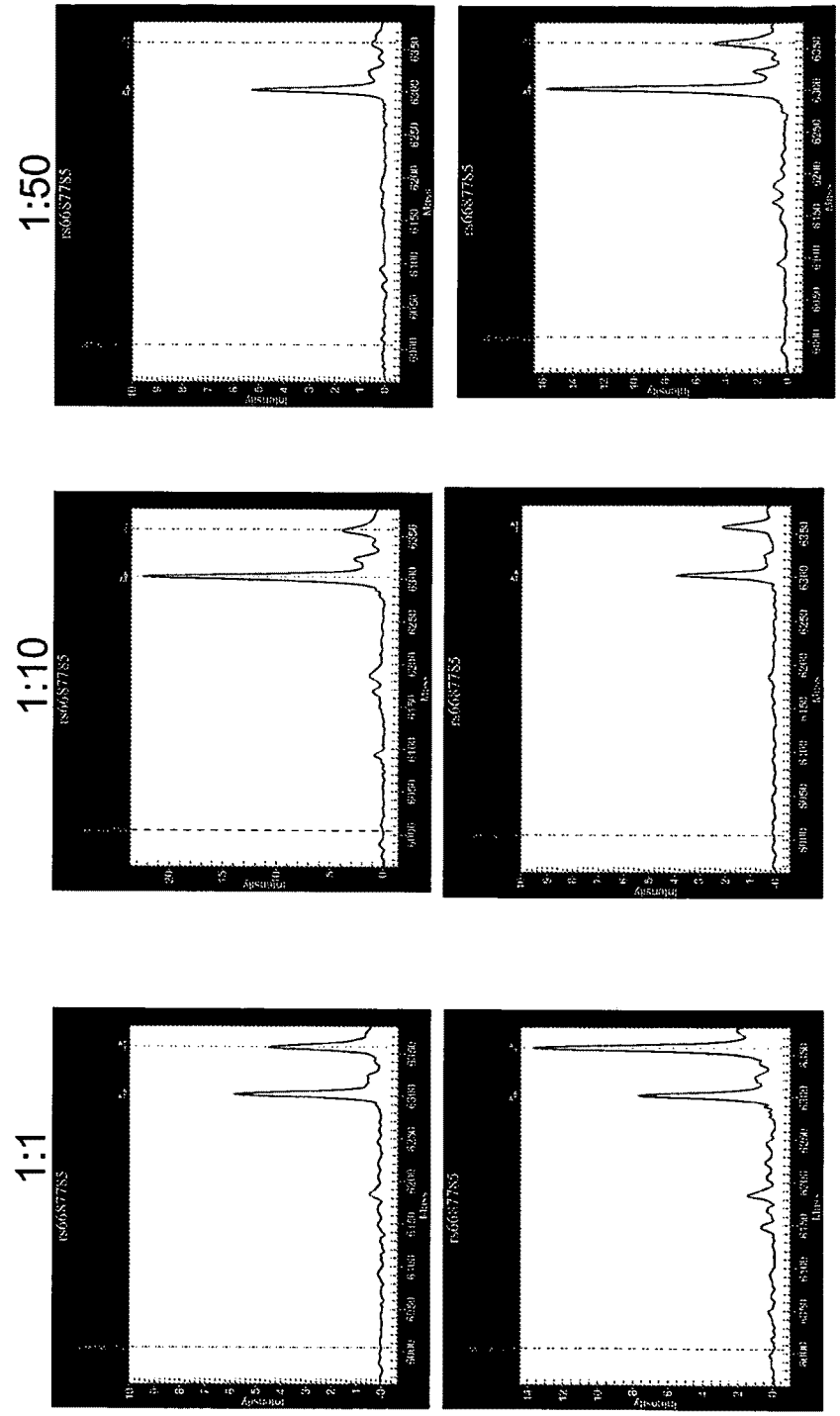

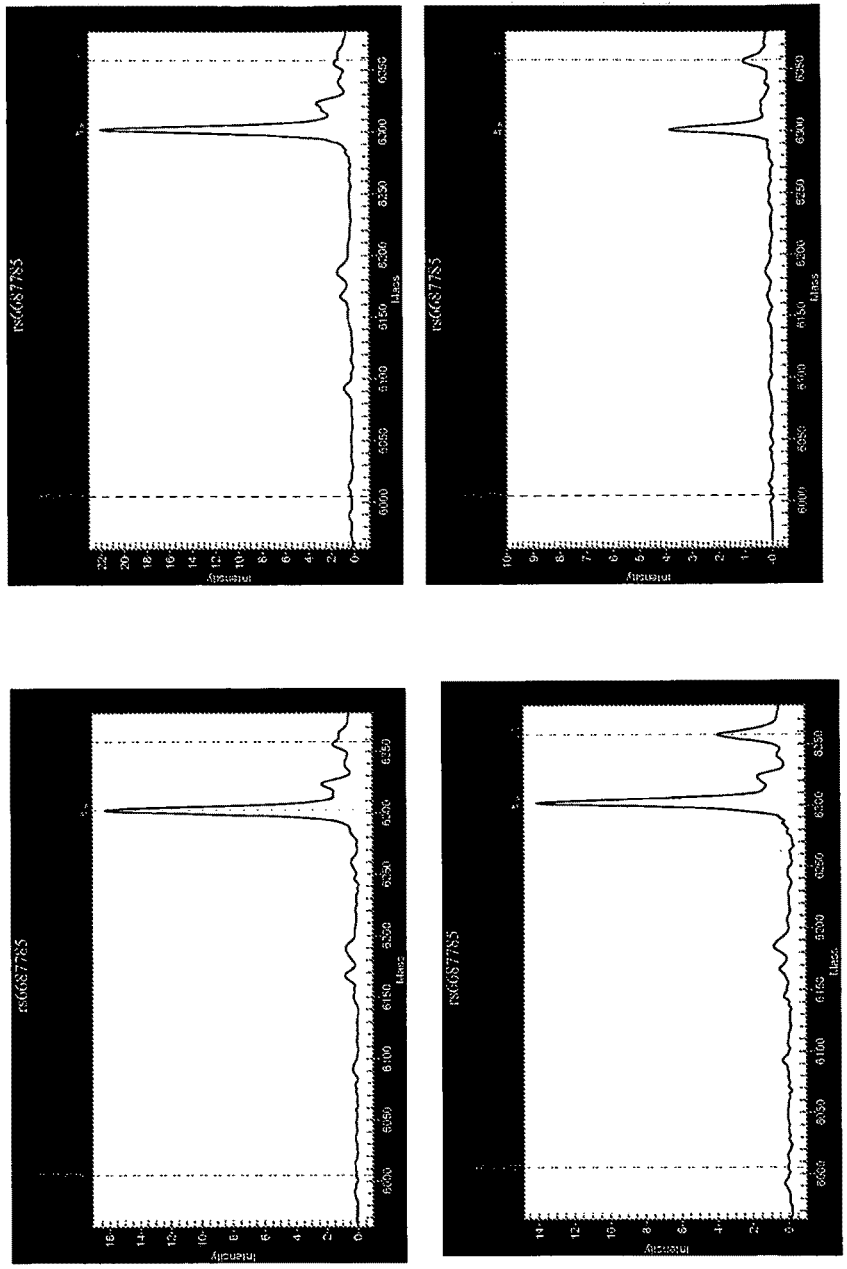

FIGURE 4A

Whole sequence: (2405bp)

SNP ID: rs6687785

Long 800bp PCR primers for generating long-stranded DNA:

Long-F-primer: 5-CCATACCCAATGCCAAGATG-3 (SEQ ID NO: 6)

Long-R-primer: 5-GATGGTGTTGATAGTGTCCC-3 (SEQ ID NO: 7)

Complement: GGGACACTATCAACACCATC (SEQ ID NO: 8)

Targets: 783 bp

Short 200bp PCR primers for generating short-stranded DNA:

Short-F-primer : 5-AAAGAGCCTCAACAGTACAC-3 (SEQ ID NO: 9)

Short-R-primer: 5-CTTTCCCATCTGGGAAATGC-3 (SEQ ID NO: 10)

Complement: GCATTTCCCAGATGGGAAAG (SEQ ID NO: 11)

Targets: 169 bp

Outside primers:

Outside-F-primer: 5- GGCGCACGCCATCACGTGCTTAAACATTGATGCAAGAC-3 (SEQ ID NO: 12)

Outside-R-primer: 5- GGCGCACGCCAAATGCCATGTTTCACTTGATGGTGTTG-3 (SEQ ID NO: 13)

Complement: CAACACCATCAAGTGAAACATGGCATT (SEQ ID NO: 14)

Targets: 478 bp

Inside Primers:

(also MassARRAY® primers)

Mass-F-primer: 5'-TCGACCCGGAGCACGTTGGATAAAGAGCCTCAACAGTACAC-3' (SEQ ID NO: 15)

Mass-R-primer: 5'-TCGACCCGGAGCACGTTGGATCTGACCTGCTTTCAAATTCA-3' (SEQ ID NO: 16)

Complement: TGAATTTGAAAGCAGGTCAGA (SEQ ID NO: 17)

Mass-Probe: CCTCAACAGTACACTTAATC (SEQ ID NO: 18)

Universal Primer:

5'-AGCGGATAACGACCCGGAGCACGTTGGAT-3' (SEQ ID NO: 19)

FIGURE 4B (SEQ ID NO: 20)

AAAAAGGAGAATAAAAAAAAGTAGAGCAAAAAGCTGCAGACTCCTTGCAGCTTTCACAATAAAGTATCCATCTCAT
AGTGTTAGTTGGTTCTAATCCTGGTGGCCTGTTCTGCAGAGTACACCAGCATTCAGTGCCACCTTGTCTACTCTGG
AGAGGGAGATGCTGCTGTGCCTGGCTTGGAATGAGCTGTTGTGCCACCCTGAGACCAAGGCAGCCACCCACAGCCC
CAACTCCATGCAAGCTCTGAACCCTAGAGCTATGGCTATTCTGTGAGTGACTGTACATTGGATGTCAGCTCTGCAG
CTGCTCTCATGTGCCCATGCTCCAGATCTTACTCTGAGGTTGCTCCATGTGTGCCCACATCATGGGCACTGGAGCC
ACTGCCACTGTAAGCTATCCAGAACCCCAGACTCTGAAGATGCTGTCACATCATGAGTGCCTGTGCTATGGACTCC
AGCTCTGTGGCTGCTCCACAAGCAACTGTGCATTAGACATTATTGCTACTACTACTAGGAGGGTGCCCACAAGCCA
TACCCAATGCCAAGATGGATCCTGTCAGCCATGACATCCCCCTTGGGTGAAAAGAGATCAGGAGTTTCCTAGCAG
CCTTATCCACCAAAGACCCCAACAGTCCTTGTTGCCACTGTGGACACCCACAGTGTCCTTAGTCATTGAATTCTCC
TGCAATATTTGCTAATGCGGACCTCACTTAGTGGGATATTCATGGAGACTACTCCCCAAAACCAGAACTGCCACAC
CCTACCCAGTTGGCATGCTTGTACCTACCTACAGGTGAATGTCTCTCCCCTCCAAAACCAGTCTATGAAGTTTAGA
ATAGGTAAATGTACCATCACGTGCTTAAACATTGATGCAAGACTACAGGAAATACAACAAATCAAGAAAACATGAC
ATCACCAAAGAAACATAATTATTTTCCAGTAGCCAGCCCCAAAGAAATGAAAATCTATAAATTGCCAGTAAAGGAA
TTTAAAATAATTGTTGTAAAGACACTCAGTGAGCTATAAGATAGCAGGTATAGAAAACTCAGTGAAATTAGAAAAA
CAATACACAAACAAAACTAGAAGTGCAACAGTGAGATGGAAGTTATAACAAAAGAACCAGACAGAAATTTTGGAAC
TGCTAAATACAATGACTGAAATGAAAAATGCTGTAAAGAGCCTCAACAGTACACTTAATC[T/A]AGCAGCAGAAA
GAATCTATGAATTTGAAAGCAGGTCAGAGGAGAAAAAAAAAGAAGAAAGAAAAAAGTGAAGAAAGCCAAACTGAGT
TATGGGACACTATCAACACCATCAAGTGAAACATGGCATTTCCCAGATGGGAAAGAGAGAGAAAGGGAGAGAGAAA
GAAAGTATTTAAAGTAATAATGGCTGAAAATTTCTCAAATCTGGAGAGAGATGCAGACATTAAAGTCCATGAAGCT
CATAGGTTTCTATACAGAATGAACTGTCTCAAAGGTAAATTAAAAAATCAGTCTCACTTACAAAAGGAGCAAAAAC
AATAAAAGACTAAGGTATAAATTTCACCAAGATAATGAAAGATCTGCACACTGAAAACTAGAAGTCATTGATGAAT
ACAATTGAAGTAGATAAATCAATGGAAAGATACCTTGTGTTCATGAATTGGAAGAATTAATATTGTTAAAATTGTC
CATACTATCTGAAACAATCCACAGATTGAATACAATCCTTATGAAAATTCCAATGACATTTTTCACAAAATGGTAA
AAAATGATTCTACGTTCTTATGGAACCACAAAGAACGCTGAATAGCCAAAAGCAACCACGAGTGAAAAGAACAAAT
CTGGAGGCATTACATTACTTGACTTCAAAATATATTACAAAGCCACAGTAATCAAAGCAGCATAATACCAGCACAA
AAACAGATATAAAGGCCAATGGAACAGAATAGAGAGCCCAGAAATAAATCCATGCATTTACAGTCAACTGATCTTC
AACAATGGTGTCAAGCATATACAATGGCAAAAGGATAGTCTCTTCAATAAATGGTGTTGGGAAACTGGATATCATC
AATGCAAAAAAGTGAAACTGGACCTCTATCTTACACCATTTACAAAAATTAACTAAAAATGGAATAAAGACTTAAA
TGTAAGATCAGAAATCGTAAAACTCTTAGAAGAAAACGTAGGGGAAAATCTTGACATTGATCTTGGCAATGATTTT
TTATGACACCAAAAGCACAGGCAACAAAGCAAAAATAAACAAATAGGACAACATCAAACTAAAAATCTTCTGTGTA
GCAAAGGAAACGATCAAGAAAATGAAAAAGCAACCTACAGAATGGGAAAAAAATAACTGCAAATATATCTGATAAG
GTGTTACTATCTAAAATATGTGAGGAACACATACAATTCAATAGCATCA

Gel Results from Genomic DNA Validation

SEQUENCE LISTING

<160> NUMBER OF SEQ ID NOS: 20

<210> SEQ ID NO 1
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
acgttggatg ctgactttt aatgattgcc attc                              34

<210> SEQ ID NO 2

```
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
acgttggatg cctaaaacca taaaaaccct agaag                              35

<210> SEQ ID NO 3
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tcgacccgga gcacgttgga tgatattagc cctttgtcag atg                    43

<210> SEQ ID NO 4
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tcgacccgga gcacgttgga tctatcatca gagtgaacag gc                     42

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
agcggataat cgacccggag cacgttggat                                   30

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ccatacccaa tgccaagatg                                              20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gatggtgttg atagtgtccc                                              20

<210> SEQ ID NO 8
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gggacactat caacaccatc                                                20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
aaagagcctc aacagtacac                                                20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ctttcccatc tgggaaatgc                                                20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gcatttccca gatgggaaag                                                20

<210> SEQ ID NO 12
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ggcgcacgcc atcacgtgct taaacattga tgcaagac                            38

<210> SEQ ID NO 13
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ggcgcacgcc aaatgccatg tttcacttga tggtgttg                            38

<210> SEQ ID NO 14
<211> LENGTH: 27
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 14
caacaccatc aagtgaaaca tggcatt                                              27

<210> SEQ ID NO 15
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tcgacccgga gcacgttgga taaagagcct caacagtaca c                              41

<210> SEQ ID NO 16
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tcgacccgga gcacgttgga tctgacctgc tttcaaattc a                              41

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
tgaatttgaa agcaggtcag a                                                    21

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 18
cctcaacagt acacttaatc                                                      20

<210> SEQ ID NO 19
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
agcggataac gacccggagc acgttggat                                            29

<210> SEQ ID NO 20
<211> LENGTH: 2401
<212> TYPE: DNA
<213> ORGANISM: Unknown
```

<220> FEATURE:
<223> OTHER INFORMATION: Description of Unknown: Genomic sequence

<400> SEQUENCE: 20

```
aaaaaggaga ataaaaaaaa gtagagcaaa aagctgcaga ctccttgcag ctttcacaat      60
aaagtatcca tctcatagtg ttagttggtt ctaatcctgg tggcctgttc tgcagagtac     120
accagcattc agtgccacct tgtctactct ggagagggag atgctgctgt gcctggcttg     180
gaatgagctg ttgtgccacc ctgagaccaa ggcagccacc cacagcccca actccatgca     240
agctctgaac cctagagcta tggctattct gtgagtgact gtacattgga tgtcagctct     300
gcagctgctc tcatgtgccc atgctccaga tcttactctg aggttgctcc atgtgtgccc     360
acatcatggg cactggagcc actgccactg taagctatcc agaacccag actctgaaga      420
tgctgtcaca tcatgagtgc ctgtgctatg gactccagct ctgtggctgc tccacaagca     480
actgtgcatt agacattatt gctactacta ctaggagggt gcccacaagc catacccaat     540
gccaagatgg atcctgtcag ccatgacatc cccttgggt gaaaagaga tcaggagttt       600
cctagcagcc ttatccacca aagaccccaa cagtccttgt tgccactgtg gacacccaca    660
gtgtccttag tcattgaatt ctcctgcaat atttgctaat gcggacctca cttagtggga    720
tattcatgga gactactccc caaaaccaga actgccacac cctacccagt tggcatgctt    780
gtacctacct acaggtgaat gtctctcccc tccaaaacca gtctatgaag tttagaatag    840
gtaaatgtac catcacgtgc ttaaacattg atgcaagact acaggaaata caacaaatca    900
agaaaacatg acatcaccaa agaaacataa ttattttcca gtagccagcc ccaaagaaat    960
gaaaatctat aaattgccag taaggaatt taaataatt gttgtaaaga cactcagtga     1020
gctataagat agcaggtata gaaaactcag tgaaattaga aaacaatac acaaacaaaa    1080
ctagaagtgc aacagtgaga tggaagttat aacaaaagaa ccagacagaa attttggaac    1140
tgctaaatac aatgactgaa atgaaaaatg ctgtaaagag cctcaacagt acacttaatc    1200
wagcagcaga aagaatctat gaatttgaaa gcaggtcaga ggagaaaaaa aaagaagaaa    1260
gaaaaaagtg aagaaagcca aactgagtta tgggacacta tcaacaccat caagtgaaac    1320
atggcatttc ccagatggga aagagagaga aaggagaga gaaagaaagt atttaaagta     1380
ataatggctg aaaatttctc aaatctggag agagatgcag acattaaagt ccatgaagct    1440
cataggtttc tatacagaat gaactgtctc aaaggtaaat taaaaaatca gtctcactta    1500
caaaaggagc aaaaacaata aaagactaag gtataaattt caccaagata atgaaagatc    1560
tgcacactga aaactagaag tcattgatga atacaattga agtagataaa tcaatggaaa    1620
gataccttgt gttcatgaat tggaagaatt aatattgtta aaattgtcca tactatctga    1680
aacaatccac agattgaata caatccttat gaaaattcca atgacatttt tcacaaaatg    1740
gtaaaaaatg attctacgtt cttatggaac cacaaagaac gctgaatagc caaaagcaac    1800
cacgagtgaa agaacaaat ctggaggcat tacattactt gacttcaaaa tatattacaa     1860
agccacagta atcaaagcag cataatacca gcacaaaaac agatataaag gccaatggaa    1920
cagaatagag agcccagaaa taatccatg catttacagt caactgatct tcaacaatgg    1980
tgtcaagcat atacaatggc aaaaggatag tctcttcaat aaatggtgtt gggaaactgg    2040
atatcatcaa tgcaaaaaag tgaaactgga cctctatctt acaccattta caaaaattaa    2100
ctaaaaatgg aataaagact taaatgtaag atcagaaatc gtaaaactct tagaagaaaa    2160
cgtaggggaa aatcttgaca ttgatcttgg caatgatttt ttatgacacc aaaagcacag    2220
```

```
gcaacaaagc aaaaataaac aaataggaca acatcaaact aaaaatcttc tgtgtagcaa    2280
aggaaacgat caagaaaatg aaaaagcaac ctacagaatg ggaaaaaaat aactgcaaat    2340
atatctgata aggtgttact atctaaaata tgtgaggaac acatacaatt caatagcatc    2400
a                                                                   2401
```

METHODS AND COMPOSITIONS FOR UNIVERSAL SIZE-SPECIFIC PCR

RELATED APPLICATIONS

This patent application is a national stage of international patent application number PCT/US2008/074692, filed on Aug. 28, 2008, which claims the benefit of U.S. Provisional Patent Application No. 60/968,878 filed on Aug. 29, 2007, entitled METHODS AND COMPOSITIONS FOR UNIVERSAL SIZE-SPECIFIC PCR, naming Min Seob Lee and Yanfeng Yang as inventors. The entire content of the foregoing patent applications are incorporated herein by reference in jurisdictions permitting such incorporation.

SEQUENCE LISTING

The instant application contains a Sequence Listing which has been submitted electronically in ASCII format and is hereby incorporated by reference in its entirety. Said ASCII copy, created on Oct. 29, 2014, is named SEQ-6014-US_S-L.txt and is 8,010 bytes in size.

FIELD OF THE INVENTION

The invention relates in part to products and processes for the amplification and detection of nucleic acids.

BACKGROUND

The isolation, detection and subsequent analysis of nucleic acids play a central role in molecular biology, and may be used, inter alia, as a starting material for diagnosis and prognosis of diseases and disorders. The recent discovery of trace amounts of short, fragmented nucleic acid in a range of biological samples, including plasma and serum, presents a new opportunity for improved, non-invasive tests. Previously, the recovery of fragmented nucleic acid from biological samples was considered unimportant, and extraction methods were designed to isolate large, undegraded nucleic acid. However, it is short base pair nucleic acid (e.g., highly degraded RNA and DNA) that offers a new source of highly informative genetic material for a wide range of applications, including prenatal diagnostics, early cancer detection and the study of apoptotic DNA from host and non-host sources.

SUMMARY OF THE INVENTION

Provided are improved methods directed to amplifying and detecting short, fragmented nucleic acid in the presence of more abundant, longer nucleic acid. These methods are simple, cost-effective and automatable in order for use in research and clinical environments.

Thus, in one aspect, the invention in part relates to the enrichment and subsequent analysis of nucleic acids based on their size. Studies have shown that the majority of cell-free nucleic acid resulting from neoplasms, allograft rejection, autoimmune reactions, fetal tissue, and the like, has a relatively small size of approximately 1,200 base pairs or less, whereas the majority of cell-free nucleic acid arising in the host from non-programmed cell death-associated events has a size greater than approximately 1,200 base pairs. In the case of cell-free fetal nucleic acid circulating in maternal plasma, the majority of fetal DNA is relatively small (approximately 500 base pairs or less), whereas the majority of circulatory, extracellular maternal DNA in maternal plasma is greater than approximately 500 base pairs. Further, in certain instances the circulatory DNA material which is smaller than approximately 500 base pairs appears to be almost entirely fetal.

The present invention in part provides products and processes for the amplification, based on size discrimination, of relatively short nucleic acid (herein referred to as "target nucleic acid") from a high background of, for example, genomic nucleic acid (herein referred to as "non-target nucleic acid"). This approach leads to a relatively enriched fraction of nucleic acid that has a higher concentration of smaller nucleic acid. The methods of the present invention, in part, lead to improved methods for detecting low copy number nucleic acid. The presence or absence of target nucleic acid or target product can be detected in a sample.

The present invention in part provides methods for amplifying a target nucleic acid from a sample containing a mixture of target and non-target nucleic acid based on the size of the nucleic acid, where the target nucleic acid size is less than the size of the non-target nucleic acid in the mixture, comprising the steps of: introducing to the sample a pair of forward and reverse inside primers that bind target and non-target nucleic acid, where the inside primers comprise both a common, universal domain and a sequence-specific domain complementary to the target and non-target nucleic acid; introducing to the sample an outside non-target binding primer, where the outside non-target binding primer anneals to non-target nucleic acid, but not target nucleic acid; introducing to the sample a universal primer capable of binding to the universal domain of the inside primers, where the universal primer is introduced at a concentration greater than the outside primer, and the outside primer is introduced at a concentration greater than the inside primer; performing an amplification reaction using a polymerase having exonuclease activity, whereby the exonuclease activity is initiated by the outside primer bound to the non-target nucleic acid and digests the inside primer bound to the same sequence, further whereby the target nucleic acid is free of outside primer and undergoes amplification initiated by the inside primers. In certain embodiments, the target nucleic acid is amplified at a higher rate than the non-target nucleic acid, thereby resulting in a sample that is selectively enriched for target nucleic acid. In certain embodiments, multiple amplification reactions are performed.

In some embodiments, provided are methods for detecting target nucleic acid, where the method further comprises detecting the presence or absence of target amplification products resulting from the method described above. Detection of said amplification products indicates the presence of said target nucleic acid in said sample. In some embodiments, either the target and/or non-target nucleic acid may be subsequently detected or analyzed after amplification.

In certain embodiments, a pair of forward and reverse outside primers are introduced, whereby both inside primers are digested during amplification. In some embodiments, one or more outside primers are introduced. In certain embodiments, the one or more outside primers preferentially anneal to non-target nucleic acid, but not target nucleic acid. In some embodiments, the one or more outside primers may also comprise a universal tag sequence that is different than the inside primer tag sequence, whereby the outside primer tag sequence is intended to bring the annealing temperature of the outside primer close to the that of inside primer. In some embodiments, the universal primer is introduced at a concentration of about 1.5, 2, 3, 4, 5, 6, 7, 8, 9, 10, 11, 12, 13, 14, 15, 20 or more times greater than the inside primers, and the outside primer is introduced at a concentration about 1.2, 1.4, 1.6, 1.8, 2.0, 2.2, 2.4, 2.6, 2.8, 3.0, 4, 5, 6, 7, 8, 9, 10 or more times greater than the inside primer. In some embodiments, the inside primers and outside primer are introduced to the sample at a concentration greater than the concentration of non-target nucleic acid.

Methods of the present invention allow for the selective enrichment of any nucleic acid less than a given size based on the placement of the outside primers. For example, outside primers designed to anneal to a non-target nucleic acid 500 base pair apart often will allow for the preferential amplification of target nucleic acid less than 500 base pair. In one embodiment of the invention, methods provided herein are used to preferentially amplify nucleic acid within the range of about 25 bases to about 10,000 bases from a sample comprising a background of longer nucleic acid. In certain embodiments, the target nucleic acid is at least about 75 base pairs, but less than about 1200 base pairs. In some embodiments, the target nucleic acid is less than 500 base pairs.

In some embodiments of the invention, the inside primers flank a locus of interest. In certain embodiments, the pair of inside primers are less than 10, 20, 30, 40, 50, 60, 70, 80, 90, 100, 150, 200, 250, 300, 350, 400, 450, 500, 550, 600, 650, 700, 800, 900, 1000, 1500 or more base pairs apart. In certain embodiments, the one or more outside primers are greater than about 100, 150, 200, 250, 300, 350, 400, 450, 500, 550, 600, 650, 700, 800, 900, 1000, 1500, 2000, 2500, 3000, 3500, 4000, 4500 or 5000 or more base pairs upstream or downstream of the locus of interest. In certain embodiments, the outside, non-target binding primers anneal to the non-target nucleic acid at least about 50, 75, 100, 150, 200, 250, 300, 350, 400, 450, 500, 550, 600, 650, 700, 800, 900, 1000, 1500, 2000, 2500, 3000, 3500, 4000, 4500 or 5000 or more base pairs upstream of the inside primer.

The present invention in part also further relates in part to a kit for amplifying target nucleic acid from a sample. The kit may comprise inside and outside primers of the invention, including, but not limited to, modified primers for amplifying target nucleic acid, universal primers, reagents for performing an amplification reaction, and instructions for performing the target nucleic acid enrichment.

The invention in part also provides methods for determining the haplotype sequence of a nucleic acid from a sample containing nucleic acids, comprising the steps of: a) introducing to the sample a pair of forward and reverse inside primers that anneal upstream and downstream of an allelic site in the haplotype, where the inside primers comprise both a common, universal domain and a sequence-specific domain complementary to the nucleic acid; b) introducing to the sample an outside allele-specific primer that anneals to an allele at another allelic site in the haplotype upstream of the allelic site of step a); c) introducing to the sample a universal primer capable of binding to the universal domain of the inside primers, where the universal primer is introduced at a concentration greater than the outside primer, and the outside primer is introduced at a concentration greater than the inside primer; d) performing multiple amplification reactions using a polymerase having exonuclease activity, whereby the exonuclease activity initiated by the outside primer digests the inside primer if the outside, allele-specific primer successfully binds to the nucleic acid, and conversely the inside primers are not digested if the outside primer does not bind to the upstream allelic site; e) determining the sequence of the allele of step a); and f) comparing the relative quantities of alleles of step a) to each other, whereby the relative quantities of alleles of step a) are indicative of the haplotype sequence comprising the allele of step b).

In certain embodiments, a pair of forward and reverse outside allele-specific primers are introduced, whereby both inside primers are digested during amplification. In some embodiments, one or more outside allele-specific primers are introduced, whereby the sequence of a haplotype comprising greater than two polymorphic sites may be determined. In some embodiments, the universal primer is introduced at a concentration about ten times greater than the inside primers, and the outside primer is introduced at a concentration about two times greater than the inside primer. In some embodiments, the inside primers and outside primer are introduced to the sample at a concentration greater than the concentration of the nucleic acid.

The invention also in part provides methods for determining the methylation status of a nucleic acid from a sample, where the nucleic acid is first treated with bisulfite to converted non-methylated cytosine to uracil. These methylation dependent sequence changes are differentiated using sequence-specific outside primers. Like the above sequencing method, the methylation status of multiple CpG sites can be determined by comparing the relative quantities of the methylated bases in step a), and comparing these quantities to a downstream marker in step b). In certain embodiments, any marker may be used in step b) to determine the methylation status of the CpG site of step a).

In some embodiments, one or more competitor oligonucleotides may be introduced to the sample at known concentrations to facilitate the quantitative analysis of target and non-target nucleic acid. In certain embodiments, the competitor oligonucleotide is the same size or nearly the same size as the target nucleic acid.

The present invention relates in part to amplifying or sequencing nucleic acids such as DNA, RNA, mRNA, miRNA, siRNA, oligonucleosomal, mitochondrial, epigenetically modified, single-stranded, double-stranded, genomic, circular, plasmid, cosmid, yeast artificial chromosomes, artificial or man-made DNA, including unique DNA sequences, and DNA that has been reverse transcribed from an RNA sample, such as cDNA, and combinations thereof. In some embodiments, the methods may be particularly useful for discriminating between RNA of varying length. In certain embodiments, the nucleic acid is cell-free nucleic acid. In some embodiments, the target nucleic acid is derived from apoptotic cells. In some embodiments, the target nucleic acid is of fetal origin, and the non-target nucleic acid is of maternal origin.

In some embodiments, the target nucleic acid comprises one or more polymorphic sites or loci of interest. In certain embodiments, the method further comprises determining the identity of at least one allele within the one or more polymorphic sites. In certain embodiments, the non-target nucleic acid also comprises the same one or more polymorphic sites, and the method further comprises determining the identity of at least one allele within the one or more polymorphic sites on the non-target nucleic acid.

In some embodiments, the methods of the present invention may be used in multiplexed reactions, where multiple target nucleic acids are amplified or sequenced in a single, multiplexed reaction. In certain embodiments, the multiple reactions are performed under identical reaction conditions. Multiplexing embodiments are particularly important when multiple regions of a target genome need to be analyzed. In one embodiment, greater than 1, 2, 3, 4, 5, 6, 7, 8, 9, 10, 11, 12, 13, 14, 15, 16, 17, 18, 19, 20, 25, 30, 35, 40, 50, 100, 200, 300, 400, 500 or more target nucleic acids are amplified, and optionally detected, or alternatively sequenced. In certain embodiments, greater than 1, 2, 3, 4, 5, 6, 7, 8, 9, 10, 11, 12, 13, 14, 15, 16, 17, 18, 19, 20, 25, 30, 35, 40, 50, 100, 200, 300, 400, 500 loci of interest are analyzed in a single reaction.

The present invention relates in part to amplifying, detecting and/or sequencing nucleic acid from a sample such as whole blood, serum, plasma, umbilical cord blood, chorionic villi, amniotic fluid, cerebrospinal fluid, spinal fluid, lavage fluid (e.g., bronchoalveolar, gastric, peritoneal, ductal, ear, arthroscopic), biopsy material (e.g., from a pre-implantation embryo), fetal nucleated cells or fetal cellular remnants isolated from maternal blood, washings of the female reproductive tract, or aspirated from a pregnant female's reproductive tract (e.g., embryonic tissues and mucous obtained from the cervix or vagina), and a sample obtained by celocentesis, urine, feces, sputum, saliva, nasal mucous, lymphatic fluid, bile, tears, sweat, breast milk, breast fluid, embryonic cells and fetal cells, or combinations thereof. In certain embodiments, the biological sample is plasma. In certain embodiments, the biological sample is cell-free or substantially cell-free. In certain embodiments, the biological sample is a sample of previously extracted, isolated or enriched nucleic acids. In some embodiments, the sample is procured by non-invasive means (e.g., maternal blood draw). In some embodiments, the sample is procured from a subject selected from the group consisting of a pregnant female, a subject suspected of suffering from or at high risk for a neoplasm, and a subject who has undergone an organ or tissue transplant or blood transfusion.

Certain methods of the present invention are particularly useful for amplifying, detecting or sequencing fetal nucleic acid from maternal plasma. In certain embodiments, the biological sample is from an animal, most preferably a human. In certain embodiments, the biological sample is from a pregnant human. In certain embodiments, the biological sample is collected from a pregnant female at 1-4, 4-8, 8-12, 12-16, 16-20, 20-24, 24-28, 28-32, 32-36, 36-40, or 40-44 weeks of fetal gestation, and preferably between 5-28 weeks of fetal gestation. In some embodiments, the pregnant female has a relatively elevated concentration of free fetal nucleic acid in her blood, plasma or amniotic fluid. In some embodiments, the pregnant female has a relatively decreased concentration of apoptotic nucleic acid in her blood, plasma or amniotic fluid. Certain methods of the present invention may be performed in conjunction with any known method to elevate fetal nucleic acid in maternal blood, plasma or amniotic fluid. Likewise, some methods of the present invention may be performed in conjunction with any known method to decrease apoptotic nucleic acid in maternal blood, plasma or amniotic fluid. In some embodiments, certain methods of the present invention may be used to amplify, detect or sequence RNA that is expressed by the fetus.

In some embodiments of the invention, the outside primers may be modified to facilitate their capture. For example, modifications include, but are not limited to, inclusion of capture mechanisms, compomers, tags, linkers and adapter molecules. Examples of compomers are described in US Patent Application Publication No. 20050287533, filed Jun. 23, 2004. Examples of adapters are described in US Patent Application Publication No. 20030211489, filed Jun. 20, 2002. Examples of capture mechanisms include, but are not limited to, biotin (which may bind, for example, to immobilized streptavidin) and hybridization or capture probes (e.g., affinity tags). Examples of capture mechanisms include, but are not limited to, one or more members of one or more binding pairs. Any suitable binding pair can be utilized to effect a non-covalent linkage, including, but not limited to, antibody/antigen, antibody/antibody, antibody/antibody fragment, antibody/antibody receptor, antibody/protein A or protein G, hapten/anti-hapten, biotin/avidin, biotin/streptavidin, folic acid/folate binding protein, FK506/FK506 binding protein, glutathione/glutathione binding protein, vitamin B12/intrinsic factor, nucleic acid/complementary nucleic acid (e.g., hybridization or capture probes; DNA, RNA, PNA). Covalent linkages also can be effected by a binding pair, such as a chemical reactive group/complementary chemical reactive group (e.g., sulfhydryl/maleimide, sulfhydryl/haloacetyl derivative, amine/isotriocyanate, amine/succinimidyl ester, and amine/sulfonyl halides). For example, a member of the binding pair is linked to a solid support in certain embodiments, and methods and conditions for attaching such binding pairs to reagents and effecting binding are known to the person of ordinary skill in the art. In some embodiments, the primer contains a universal binding oligonucleotide capable of hybridizing to a capture probe.

In some embodiments, a solid support is introduced to the sample, or alternatively the sample is stored in a solid support capable of binding nucleic acid. In one embodiment, the solid support is adapted to bind nucleic acids. The solid support may be selected from, for example, the following: paramagnetic microparticles, silica gel, silica particles, controlled pore glass, magnetic beads, biomagnetic separation beads, microspheres, divinylbenzene (DVB) resin, cellulose beads, capillaries, filter membranes, columns, nitrocellulose paper, flat supports, arrays, glass surfaces, fiber optic arrays, metal surfaces, plastic materials, polycarbonate materials, multi-well plates or membranes, wafers, combs, pins and needles, or combination thereof (for example, wells filled with beads). In certain embodiments, the solid support is a hydroxyl donor (e.g., silica or glass) or contains a functional group that serves as a hydroxyl donor and is attached to a solid support. In certain embodiments, the solid support is a silica gel membrane.

In certain embodiments, the solid support has a functional group-coated surface. In certain embodiments, the functional group-coated surface is silica-coated, hydroxyl coated, amine-coated, carboxyl-coated or encapsulated carboxyl group-coated, for example. A bead may be silica-coated or a membrane may contain silica gel in certain embodiments.

In some embodiments, the solid support is removed from the sample using a method selected from the group consisting of applying a magnetic field, applying vacuum filtration and centrifugation. In certain embodiments, paramagnetic beads are separated from the sample using magnets or magnetic devices.

In some embodiments, the outside and/or inside primers contain a label. Primers may be labeled with any type of chemical group or moiety that allows for detection including, but not limited to, radioactive molecules, fluorescent molecules, antibodies, antibody fragments, haptens, carbohydrates, biotin, derivatives of biotin, phosphorescent moieties, luminescent moieties, electrochemiluminescent moieties, chromatic moieties, and moieties having a detectable electron spin resonance, electrical capacitance, dielectric constant or electrical conductivity, or any combination of labels thereof. The primers can be labeled with one or more chemical groups or moieties. Each primer can be labeled with the same chemical group or moiety. Alternatively, each different primer can be labeled with a different chemical group or moiety. The labeled primers can be dNTPs, ddNTPs, or a mixture of both dNTPs and ddNTPs. The unlabeled primers can be dNTPs, ddNTPs or a mixture of both dNTPs and ddNTPs. In some embodiments, the label is only detectable when the primer is bound to nucleic acid.

In some embodiments, the invention in part provides methods for amplifying, detecting or sequencing a nucleic acid, which may be performed prior to, subsequent to, or simultaneously with one or more other methods for selectively separating, enriching or extracting nucleic acid. Examples of other methods for separating, enriching or extracting nucleic acid include, but are not limited to, electrophoresis, liquid chromatography, size exclusion, microdialysis, electrodialysis, centrifugation, centrifugal membrane exclusion, restriction enzyme-based methods, organic or inorganic extraction, affinity chromatography, PCR, genome-wide PCR, sequence-specific PCR, methylation-specific PCR, restriction endonuclease enhanced polymorphic sequence detection, introducing a silica membrane or molecular sieve, nanopore-based methods, fragment selective amplification, or combinations thereof. Examples of separating, enriching or extracting methods are also provided in PCT Patent Application Publication No. PCT/US07/69991, filed May 30, 2007.

The methods provided herein may also be modified to introduce additional steps, for example, in order to improve the amplification of nucleic acid or improve analysis of target nucleic acid following amplification. For example, the sample may be first lysed in the presence of a lysis buffer, which may comprise a chaotropic agent (e.g., salt), a proteinase, a protease or a detergent, or combinations thereof, for example. Chaotropic agents may be added to the sample to improve the binding of the non-target nucleic acid to the nucleic acid-binding solid support, where the longer, non-target nucleic acid is more likely to bind to the solid support than the shorter, target nucleic acid. In an embodiment of the invention, the chaotropic agent is selected from the group consisting of guanidine salt, sodium iodide, potassium iodide, sodium thiocyanate, urea, sodium chloride, magnesium chloride, calcium chloride, potassium chloride, lithium chloride, barium chloride, cesium chloride, ammonium acetate, sodium acetate, ammonium perchlorate and sodium perchlorate. In certain embodiments, the salt is a guanidine salt, most preferably guanidine (iso)thiocyanate, or is a sodium salt, most preferably sodium perchlorate. In the methods provided herein, the chaotropic agent is introduced at a concentration sufficient to bind non-target nucleic acid to a solid support.

In some embodiments, methods that comprise target nucleic acid binding to a solid support may further include adding a washing step or steps to remove non-nucleic acid from the solid-support-target nucleic acid complex. In some embodiments, the solid support-nucleic acid complex is further washed successively with a wash buffer and one or more alcohol-water solutions, and subsequently dried. In certain embodiments, the wash buffer comprises a chaotropic agent (e.g., salt), and optionally, a carrier such as LPA, RNA, tRNA, dextran blue, glycogen or polyA RNA, for example.

In some embodiments, the invention in part further comprises an additional amplification step, for example, after the target nucleic acid is first preferentially amplified. In one embodiment of the invention, the target nucleic acid is amplified by a target-specific amplification method such as allele-specific PCR. In some embodiments, all of the remaining nucleic acid (e.g., the target nucleic acid remaining after the non-target nucleic acid has been removed) are amplified with a common set of universal PCR primers.

The size-based analysis of the present invention in part permits the analysis of fetal genetic traits including those involved in chromosomal aberrations (e.g. aneuploidies or chromosomal aberrations associated with Down's syndrome) or hereditary Mendelian genetic disorders and, respectively, genetic markers associated therewith (e.g. single gene disorders such as cystic fibrosis or the hemoglobinopathies). Size-specific amplification of extracellular fetal DNA in the maternal circulation thus facilitates the non-invasive detection of fetal genetic traits, including paternally inherited sequence variations. Thus, in some embodiments of the invention, methods further comprise analyzing the non-target nucleic acid, the target nucleic acid or both the non-target and target nucleic acid. Examples of nucleic acid analysis include, but are not limited to, genotype analysis, sequencing analysis, methylation analysis, quantitative analysis and qualitative analysis.

In some embodiments, processes of the present invention are extremely sensitive and allow the detection of low copy number target nucleic acid that are in various ratios (relative to non-target nucleic acid) including but not limited to about 1:1, 1:2, 1:3, 1:4, 1:5, 1:6-1:10, 1:11-1:20, 1:21-1:30, 1:31-1:40, 1:41-1:50, 1:51-1:60, 1:61-1:70, 1:71-1:80, 1:81-1:90, 1:91:1:100, 1:101-1:200, 1:250, 1:251-1:300, 1:301-1:400, 1:401-1:500, 1:501-1:600, 1:601-1:700, 1:701-1:800, 1:801-1:900, 1:901-1:1000, 1:1001-1:2000, 1:2001-1:3000, 1:3001-1:4000, 1:4001-1:5000, 1:5001-1:6000, 1:6001-1:7000, 1:7001-1:8000, 1:8001-1:9000, 1:9001-1:10,000; 1:10,001-1:20,000, 1:20,001:1:30,000, 1:30,001-1:40,000, 1:40,001-1:50,000, and greater than 1:50,000.

In some embodiments, methods of the present invention result in a final relative percentage of target nucleic acid to non-target nucleic acid of at least about 5%, 10%, 15%, 20%, 25%, 30%, 35%, 40%, 45%, 50%, 55%, 60%, 65%, 70%, 75%, 80%, 85%, 90%, 95% or more.

BRIEF DESCRIPTION OF THE DRAWINGS

FIG. 1 is a schematic representation of a universal size specific amplification embodiment used to preferentially amplify short target nucleic acid. Exemplary relative primer concentrations for the inside, outside and universal primers is shown as 1:2:10.

FIGS. 3A and 3B are a series of mass spectrograms that shows the successful enrichment of the low copy number, small nucleic acid (200 base pair) in the presence of the high copy number amplicon (800 base pair). The series of mass spectrograms that shows the successful enrichment of low copy number short nucleic acid in a heterogeneous mixture of nucleic acid at different concentrations. The different concentrations (1:1, 1:10, 1:50, 1:100 and 1:200) represent different ratios of small to large nucleic acid fragments. As the Figures illustrate, the low concentration small fragments are either hard to detect (1:50 ratio) or not detectable (1:100 and 1:200) before the preferential amplification of the small fragments (see "Standard PCR" rows which corresponds to amplification in the presence of only the inside primers, but no outside primers). However, after the short fragments are amplified using certain methods of the present invention (see "USS-PCR rows, which correspond to amplification in the presence of both the inside and outside primers), the small fragments are detectable while the large fragment peaks have decreased in size.

FIGS. 4A and 4B provide sequences of inside (SEQ ID NOS: 15-18, respectively, in order of appearance) and outside (SEQ ID NOS: 12-14, respectively, in order of appearance) primers, universal (SEQ ID NO: 19) primers and a genomic sequence (SEQ ID NO: 20) that comprises the target and non-target sequences, as described in the Examples. Long primers are disclosed as SEQ ID NOS: 6-8 and short primers are disclosed as SEQ ID NOS: 9-11, respectively, in order of appearance.

DETAILED DESCRIPTION OF THE INVENTION

Figure 2A:
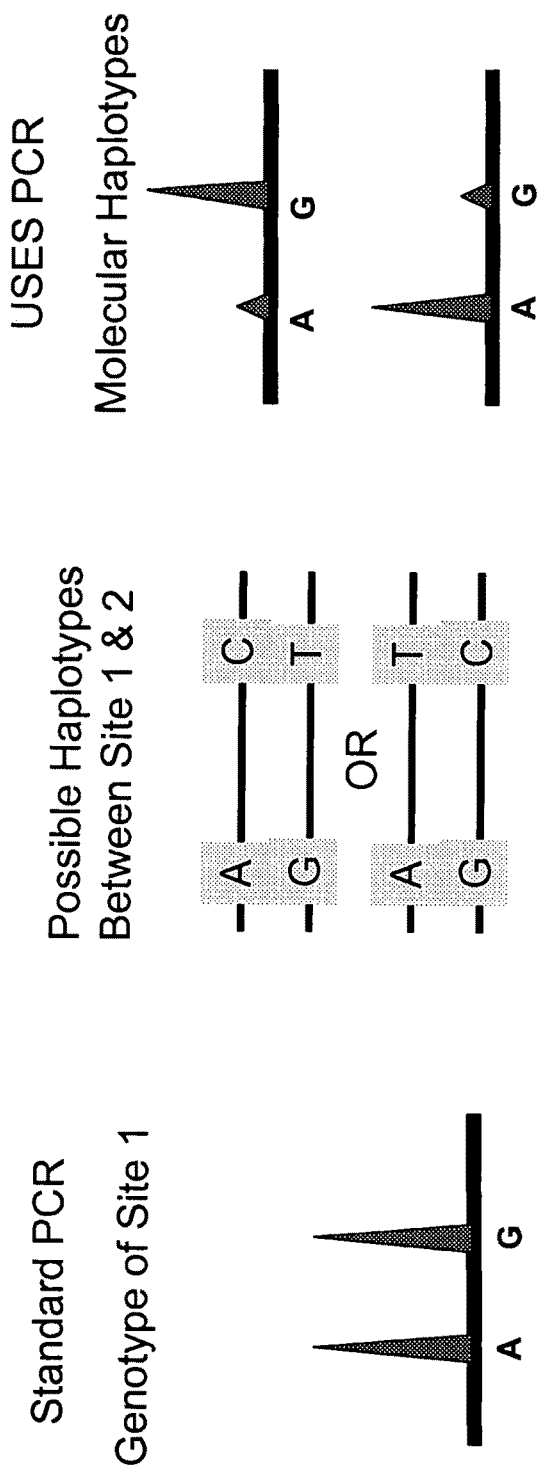
FIGS. 2A and 2B are schematic representations of a universal sequence specific amplification embodiment used to sequence nucleic acid. In this embodiment, preferential amplification occurs when the inside primer is not digested by the exonuclease activity of the polymerase initiated at the outside primer location. However, when an allele-specific match occurs at the outside primer location, the polymerase is able to initiate exonuclease activity and digest the inside primer, thereby eliminating the inside primer effects and decreasing the rate of amplification (low amplification). The results of these two different scenarios are illustrated in FIG. 2A.

The presence of short, fragmented cell-free nucleic acid in peripheral blood is a well established phenomenon. Cell-free nucleic acid may originate from a number of sources, including programmed cell death—also known as apoptosis. The source of nucleic acid that arise as a result of apoptosis may be found in many body fluids and originate from several sources, including, but not limited to, normal programmed cell death in the host, induced programmed cell death in the case of an autoimmune disease, septic shock, neoplasms (malignant or non-malignant), or non-host sources such as an allograft (transplanted tissue), or the fetus or placenta of a pregnant woman. The applications for the amplification, detection and sequencing of extracellular nucleic acid from peripheral blood or other body fluids are widespread and may include inter alia, non-invasive prenatal diagnosis, cancer diagnostics and prognostics, pathogen detection, auto-immune response detection and detection of allograft rejection.

In a particular embodiment of the invention, methods provided herein may be used to enrich for nucleic acid of fetal origin in a maternal sample. It is well established that fetal nucleic acid is present in maternal plasma from the first trimester onwards, with concentrations that increase with progressing gestational age (Lo et al. Am J Hum Genet (1998) 62:768-775). After delivery, fetal nucleic acid is cleared very rapidly from the maternal plasma (Lo et al. Am J Hum Genet (1999) 64:218-224). Fetal nucleic acid is present in maternal plasma in a much higher fractional concentration than fetal nucleic acid in the cellular fraction of maternal blood (Lo et al. Am J Hum Genet (1998) 62:768-775). Thus, in some embodiments, the target nucleic acid is of fetal origin, the non-target nucleic acid is of maternal origin and the sample is maternal plasma.

The present invention in part includes products and processes to amplify, detect and sequence short base pair nucleic acid in the presence of a high background of genomic material (e.g., host or maternal nucleic acids). More specifically, the present invention in part provides products and processes for the relative enrichment, based on size-specific amplification, of nucleic acid of approximately 500 base pairs or less (herein referred to as "target nucleic acid") in a high background of genomic nucleic acids (herein referred to as "non-target nucleic acid"). The products and processes rely in part on the use of amplification reactions (e.g., PCR) initiated by specifically-placed primers at varying concentrations to preferentially amplify target nucleic acid in a high background of non-target nucleic acid.

Polymerase chain reaction (PCR) is a method whereby virtually any DNA sequence can be selectively amplified. The method involves using paired sets of oligonucleotides of predetermined sequence that hybridize to opposite strands of DNA and define the limits of the sequence to be amplified. The oligonucleotides prime multiple sequential rounds of DNA synthesis catalyzed by a DNA polymerase. Each round of synthesis is typically separated by a melting and re-annealing step, allowing a given DNA sequence to be amplified several hundred-fold in less than an hour (Saiki et al., Science 239:487, 1988).

The simplicity and reproducibility of these reactions has given PCR broad applicability. For example, PCR has gained widespread use for the diagnosis of inherited disorders and susceptibility to disease. Typically, the genomic region of interest is amplified from either genomic DNA or from a source of specific cDNA encoding the cognate gene product. Mutations or polymorphisms are then identified by subjecting the amplified DNA to analytical techniques such as DNA sequencing, hybridization with allele specific oligonucleotides, restriction endonuclease cleavage or single-strand conformational polymorphism (SSCP) analysis. The methods of the present invention can take advantage of amplification primers placed at varying distances from said mutation or sequence variations, wherein inside primers with universal domains (or tags) are present at high concentrations and drive the amplification process. However, the placement of outside primers that preferentially bind upstream of the inside primers on longer, non-target nucleic acid facilitate the digestion of the inside primers via the exonuclease activity of amplification enzymes (e.g., DNA polymerases). Without the inside primers, the non-target nucleic acid is amplified at a slower rate than the target nucleic acid, and the target nucleic acid is thereby relatively enriched compared to the non-target nucleic acid.

The term "extraction" as used herein refers to the partial or complete separation, and optionally isolation, of a nucleic acid from a biological or non-biological sample comprising other nucleic acids. The terms "selective" and "selectively" as used herein refer to the ability to extract a particular species of nucleic acid molecule, on the basis of molecular size, from a sample that comprises a mixture of nucleic acid molecules. In one embodiment of the invention, the target or non-target nucleic acid may be extracted from a sample. For example, in order to extract non-target nucleic acid, the outside primer may be labeled, for example with biotin, and selectively extracted from the sample.

The terms "nucleic acid" and "nucleic acid molecule" as used herein may be used interchangeably throughout the disclosure. The terms refer to oligonucleotides, oligos, polynucleotides, deoxyribonucleotide (DNA), genomic DNA, mitochondrial DNA (mtDNA), complementary DNA (cDNA), bacterial DNA, viral DNA, viral RNA, RNA, micro RNA (miRNA), message RNA (mRNA), transfer RNA (tRNA), ribosomal RNA (rRNA), siRNA, catalytic RNA, clones, plasmids, M13, P1, cosmid, bacteria artificial chromosome (BAC), yeast artificial chromosome (YAC), amplified nucleic acid, amplicon, PCR product and other types of amplified nucleic acid, RNA/DNA hybrids and polyamide nucleic acids (PNAs), all of which can be in either single- or double-stranded form, and unless otherwise limited, would encompass known analogs of natural nucleotides that can function in a similar manner as naturally occurring nucleotides and combinations and/or mixtures thereof. Thus, the term "nucleotides" refers to both naturally-occurring and modified/non-naturally-occurring nucleotides, including nucleoside tri, di, and monophosphates as well as monophosphate monomers present within polynucleic acid or oligonucleotide. A nucleotide may also be a ribo; 2'-deoxy; 2',3'-deoxy as well as a vast array of other nucleotide mimics that are well-known in the art. Mimics include chain-terminating nucleotides, such as 3'-O-methyl, halogenated base or sugar substitutions; alternative sugar structures including nonsugar, alkyl ring structures; alternative bases including inosine; deaza-modified; chi, and psi, linker-modified; mass label-modified; phosphodiester modifications or replacements including phosphorothioate, methylphosphonate, boranophosphate, amide, ester, ether; and a basic or complete internucleotide replacements, including cleavage linkages such a photocleavable nitrophenyl moieties.

The term "target nucleic acid" as used herein refers to the nucleic acid of interest that is amplified, detected or sequenced based on its molecular size. In a preferred embodiment, the target nucleic acid has a molecular size smaller than the non-target nucleic acid present in the biological sample, for example, smaller than about 500 base pairs. In a related embodiment, the target nucleic acid is fetal DNA, oncogenic DNA, or any non-host DNA (eg, pathogenic). In another related embodiment, the target nucleic acid is cell-free nucleic acid. In another related embodiment, the target nucleic acid is oligonucleosomal nucleic acid generated during programmed cell death.

The term "non-target nucleic acid" as used herein refers to the relatively high amount of background nucleic acid present in a sample. In certain embodiments, non-target nucleic acid has a molecular size larger than target nucleic acid, for example, greater than about 500 base pairs. In a related embodiment, non-target nucleic acid is from a host or host cell. In certain embodiments, non-target nucleic acid is of maternal origin. In some embodiments, the non-target nucleic acid is separated or extracted from the sample, thereby yielding a relatively enriched target nucleic acid sample. In some embodiments, the non-target nucleic acid is genomic DNA.

The term "molecular size" as used herein refers to the size of a nucleic acid molecule, which may be measured in terms of a nucleic acid molecule's mass or length (bases or base pairs).

The term "sample" as used herein includes a specimen or culture (e.g., microbiological cultures) that includes nucleic acids. A sample may include a specimen of synthetic origin (eg, competitor oligonucleotide). Biological samples include whole blood, serum, plasma, umbilical cord blood, chorionic villi, amniotic fluid, cerebrospinal fluid, spinal fluid, lavage fluid (e.g., bronchoalveolar, gastric, peritoneal, ductal, ear, arthroscopic), biopsy material from a pre-implantation embryo, fetal nucleated cells or fetal cellular remnants isolated from maternal blood, urine, feces, sputum, saliva, nasal mucous, lymphatic fluid, bile, tears, sweat, breast milk, breast fluid, washings of the female reproductive tract and a sample obtained by celocentesis, cervical mucosa, embryonic cells and fetal cells. In certain embodiments, the sample comprises a mixture of nucleic acids. For example, the mixture may comprise nucleic acid from different species or from different individuals. In a further embodiment, the biological sample contains cellular elements or cellular remnants in maternal blood.

In one embodiment, the sample is from a pregnant female. In a related embodiment, the sample is procured through non-invasive means (e.g., a blood draw). The term "non-invasive" as used herein refers a method for collecting a sample that poses minimal risk to an individual (e.g., the mother, fetus, victim, and the like). An example of a non-invasive method is a blood draw; whereas examples of invasive methods include amniocentesis and chorionic villus sampling, both of which constitute a finite risk to the fetus. In another related embodiment, the sample is cervical mucosa, which is obtained, for example, by an aspiration catheter.

In certain embodiments, the biological sample is blood, and more preferably plasma. As used herein, the term "blood" encompasses whole blood or any fractions of blood, such as serum and plasma as conventionally defined. Blood plasma refers to a fraction of whole blood, which may result from centrifugation of blood treated with anticoagulants. Blood serum refers to the watery portion of fluid remaining after a blood sample has coagulated. These examples are not to be construed as limiting the sample types applicable to the present invention.

In a preferred method, blood handling protocols often are followed to ensure minimal degradation of nucleic acid in the sample and to minimize the creation of apoptotic nucleic acid in the sample. Blood handling methods are well known in the art.

In certain embodiments, the biological sample is cell-free or substantially cell-free. In a related embodiment, the biological sample is a sample containing previously extracted, isolated or purified nucleic acids. One way of targeting target nucleic acid is to use the non-cellular fraction of a biological sample; thus limiting the amount of intact cellular material (e.g., large strand genomic DNA) from contaminating the sample. In an embodiment of the invention, a cell-free sample (such as pre-cleared plasma, urine, and the like) is first treated to inactivate intracellular nucleases through the addition of an enzyme, a chaotropic substance, a detergent or any combination thereof. In some embodiments, the biological sample is first treated to remove substantially all cells from the sample by any of the methods known in the art, for example, centrifugation, filtration, affinity chromatography, and the like.

In some embodiments, a cell lysis inhibitor is introduced to the sample. In some embodiments, lysis may be blocked. In these embodiments, the sample may be mixed with an agent that inhibits cell lysis to inhibit the lysis of cells, if cells are present, where the agent is a membrane stabilizer, a cross-linker, or a cell lysis inhibitor. In some of these embodiments, the agent is a cell lysis inhibitor such as glutaraldehyde, derivatives of glutaraldehyde, formaldehyde, formalin, or derivatives of formaldehyde. See U.S. patent application 20040137470, which is hereby incorporated by reference, for examples of methods relating to the use of cell lysis inhibitors.

Known methods for nucleic acid isolation or extraction from blood, plasma, or serum can be performed prior to, after, or in combination with certain methods of the present invention. Any standard DNA or RNA isolation technique can be used to isolate nucleic acid including, but not limited to, QIAamp DNA Blood Midi Kit supplied by QIAGEN. Other standard methods of DNA isolation are described, for example, in (Sambrook et al., Molecular Biology: A laboratory Approach, Cold Spring Harbor, N.Y. 1989; Ausubel, et al., Current protocols in Molecular Biology, Greene Publishing, Y, 1995). A preferred method for isolation of plasma DNA is described in Chiu et al., 2001, Clin. Chem. 47: 1607-1613, which is herein incorporated by reference in its entirety. Other suitable methods are provided in Example 2 of PCT International Application Publication Number 2007/028155, filed on Sep. 1, 2006; PCT International Application Number PCT/US07/69991, filed May 31, 2007; U.S. Provisional Application No. 60/805,073, filed Jun. 16, 2006; and U.S. Provisional Application No. 60/908,167, filed Mar. 26, 2007.

Certain methods of the present invention may further comprise analyzing the non-target nucleic acid, the target nucleic acid or both the non-target and target nucleic acid prior to, after, or in combination with the amplification, detection or sequencing methods of the present invention. Examples of analyzing a nucleic acid may include, but are not limited to, genotyping, sequencing, quantitative analysis and qualitative analysis. Nucleic acid analysis methods known in the art include, for example, PCR, allele specific PCR, gel electrophoresis, ELISA, mass spectrometry, MALDI-TOF mass spectrometry hybridization, primer extension or microsequencing methods, ligase sequence determination methods (e.g., U.S. Pat. Nos. 5,679,524 and 5,952,174, and WO 01/27326), mismatch sequence determination methods (e.g., U.S. Pat. Nos. 5,851,770; 5,958,692; 6,110,684; and 6,183, 958), allele specific oligonucleotide (ASO) analysis, methylation-specific PCR (MSPCR), pyrosequencing analysis, acycloprime analysis, Reverse dot blot, Dynamic allele-specific hybridization (DASH), Peptide nucleic acid (PNA) and locked nucleic acids (LNA) probes, Molecular Beacons, Intercalating dye, fluorescence detection, fluorescence resonance energy transfer (FRET), FRET primers, AlphaScreen, SNPstream, genetic bit analysis (GBA), Multiplex minisequencing, SNaPshot, GOOD assay, Microarray miniseq, arrayed primer extension (APEX), Microarray primer extension, Tag arrays, Coded microspheres, Template-directed incorporation (TDI), fluorescence polarization, Colorimetric oligonucleotide ligation assay (OLA), Sequence-coded OLA, Microarray ligation, Ligase chain reaction, Padlock probes, and Invader assay, microarray sequence determination methods, restriction fragment length polymorphism (RFLP) procedures, single primer linear nucleic acid amplification, as described in U.S. Pat. No. 6,251,639, PCR-based assays (e.g., TAQMAN® PCR System (Applied Biosystems)), nucleotide sequencing methods, hybridization methods, conventional dot blot analyses, single strand conformational polymorphism analysis (SSCP, e.g., U.S. Pat. Nos. 5,891,625 and 6,013,499; Orita et al., Proc. Natl. Acad. Sci. U.S.A 86: 27776-2770 (1989)), BeadArray, Invader assay, denaturing gradient gel electrophoresis (DGGE), heteroduplex analysis, mismatch cleavage detection, and techniques described in Sheffield et al., Proc. Natl. Acad. Sci. USA 49: 699-706 (1991), White et al., Genomics 12: 301-306 (1992), Grompe et al., Proc. Natl. Acad. Sci. USA 86: 5855-5892 (1989), and Grompe, Nature Genetics 5: 111-117 (1993), detection by mass spectrometry, for example Sequenom Inc.'s primer extension method (e.g., iPLEX™) or MassCLEAVE® assay (information regarding these and other Sequenom assays may be found at, for example, the sequenom.com website on the World Wide Web), real time-PCR (e.g., U.S. Pat. No. 5,210,015, U.S. Pat. No. 5,487,972), or hybridization with a suitable nucleic acid primer specific for the sequence to be detected. Suitable nucleic acid primers can be provided in a format such as a gene chip, bead, or any combination thereof.

The target nucleic acid can be detected by a variety of methods including but not limited to fluorescence detection, DNA sequencing gel, capillary electrophoresis on an automated DNA sequencing machine, microchannel electrophoresis, and other methods of sequencing, mass spectrometry, time of flight mass spectrometry, quadrupole mass spectrometry, magnetic sector mass spectrometry, electric sector mass spectrometry infrared spectrometry, ultraviolet spectrometry, palentiostatic amperometry or by DNA hybridization techniques including Southern Blots, Slot Blots, Dot Blots, and DNA microarrays, wherein DNA fragments would be useful as both "probes" and "targets," ELISA, fluorimetry, Fluorescence Resonance Energy Transfer (FRET), SNP-IT, GeneChips, HuSNP, BeadArray, TaqMan assay, Invader assay, MassExtend®, or MassCleave® method.

As used herein, the term "genotype" refers to the identity of alleles, sequence variations or non-homologous variants present in an individual or sample. The term "genotyping a sample" or "genotyping an individual" refers to determining a specific allele or specific nucleotide(s) or sequence variation(s) in a sample or carried by an individual at particular region(s) (eg, polymorphic sites or loci of interest).

As used herein, an "allele" is one of several alternate forms of a gene or non-coding regions of nucleic acid that occupy the same position on a chromosome. The term "allele" can be used to describe nucleic acid from any organism including but not limited to bacteria, viruses, fungi, protozoa, molds, yeasts, plants, humans, non-humans, animals, and archeabacteria.

Alleles can have the identical sequence or can vary by a single nucleotide (SNP) or more than one nucleotide. With regard to organisms that have two copies of each chromosome, if both chromosomes have the same allele, the condition is referred to as homozygous. If the alleles at the two chromosomes are different, the condition is referred to as heterozygous. For example, if the locus of interest is SNP X on chromosome 1, and the maternal chromosome contains an adenine at SNP X (A allele) and the paternal chromosome contains a guanine at SNP X (G allele), the individual is heterozygous at SNP X.

The term "sequence variation" as used herein refers to an allelic variant. Sequence variations can include single nucleotide polymorphisms (SNP's) as well as simple sequence length polymorphisms. A sequence variation can be due to one or more nucleotide substitutions at one allele in comparison to another allele or can be due to an insertion or deletion, duplication, inversion and other alterations known to the art. Other sequence variations include, but are not limited to, restriction fragment length polymorphisms (RFLPs), polymorphisms, mutations, insertions/deletions, short tandem repeats, such as di-, tri- or tetra-nucleotide repeats (STRs), copy number variations, and the like. As used herein, sequence variation may include epigenetic variants, as long as cleavage by non-epigenetic-specific cleavage agents is used.

The term "amplification reaction" refers to any in vitro means for multiplying the copies of nucleic acid. An amplification reaction can be either exponential or linear. As used herein, the term "preferentially amplified" refers to an amplification reaction that occurs at a faster rate than a non-preferentially amplified reaction. For example, a target nucleic acid with a higher concentration of amplification primers will be amplified at a faster rate than a non-target nucleic acid with a lower concentration of amplification primers. Also, a target nucleic acid with the benefit a high concentration of forward and reverse universal tag primers will be amplified at a faster rate than a non-target nucleic acid with only one or fewer forward or reverse universal tag primers.

"Amplifying" refers to a step of submitting a sample to conditions sufficient to allow for amplification. Components of an amplification reaction may include, but are not limited to, for example, primers, a polynucleotide template, polymerase, nucleotides, dNTPs and the like. The term "amplifying" typically refers to an "exponential" increase in target nucleic acid. However, "amplifying" as used herein can also refer to linear increases in the numbers of a select target sequence of nucleic acid, but is different than a one-time, single primer extension step. In certain embodiments of the invention, the polymerase has exonuclease activity.

"Polymerase chain reaction" or "PCR" refers to a method whereby a specific segment or subsequence of a target double-stranded DNA, is amplified in a geometric progression. PCR is well known to those of skill in the art; see, e.g., U.S. Pat. Nos. 4,683,195 and 4,683,202; and PCR Protocols: A Guide to Methods and Applications, Innis et al., eds, 1990.

"Universal tag" and "universal domain" may be used interchangeably throughout this disclosure. Both terms refer to a common portion of a primer sequence that is not complementary to a target or non-target nucleic acid sequence. Instead, the universal domain is complementary to a universal primer.

As used herein, a "universal primer" refers to a primer that binds to the universal domain and initiates the simultaneous amplification of any nucleic acid with a universal domain under a single set of reaction conditions. In certain embodiments of the invention, the universal primer is introduced at a concentration greater than the inside and outside primers.

"Oligonucleotide" as used herein refers to linear oligomers of natural or modified nucleosidic monomers linked by phosphodiester bonds or analogs thereof. Oligonucleotides include deoxyribonucleosides, ribonucleosides, anomeric forms thereof, peptide nucleic acids (PNAs), and the like, capable of specifically binding to a target nucleic acid. Usually monomers are linked by phosphodiester bonds or analogs thereof to form oligonucleotides ranging in size from a few monomeric units, e.g., 3-4, to several tens of monomeric units, e.g., 40-60. Whenever an oligonucleotide is represented by a sequence of letters, such as "ATGCCTG," it will be understood that the nucleotides are in 5'-3' order from left to right and that "A" denotes deoxyadenosine, "C" denotes deoxycytidine, "G" denotes deoxyguanosine, "T" denotes deoxythymidine, and "U" denotes the ribonucleoside, uridine, unless otherwise noted. Usually oligonucleotides comprise the four natural deoxynucleotides; however, they may also comprise ribonucleosides or non-natural nucleotide analogs. Where an enzyme has specific oligonucleotide or polynucleotide substrate requirements for activity, e.g., single stranded DNA, RNA/DNA duplex, or the like, then selection of appropriate composition for the oligonucleotide or polynucleotide substrates is well within the knowledge of one of ordinary skill.

As used herein, the terms "primer", "oligonucleotide primer" and "probe" are interchangeable when used to discuss an oligonucleotide that anneals to a nucleic acid. In amplification embodiments of the invention, an oligonucleotide primer serves as a point of initiation of nucleic acid synthesis. In certain embodiments, oligonucleotide primers may not be used solely for nucleic acid synthesis. Rather, they may be used as probes to selectively bind to non-target nucleic acid and to "fish out" or otherwise isolate the nucleic acid to which it is annealed. Primers can be a variety of lengths and are often less than 50 nucleotides in length, for example 12-25 nucleotides in length. The length and sequences of primers for use in the invention can be designed based on principles known to those of skill in the art.

As used herein, "inside primer" refers to a primer that binds target and non-target nucleic acid and contains both a sequence-specific domain complementary to the target or non-target nucleic acid and a common universal domain. Inside primers are designed to bind closer to sequence variations than outside primers. See FIG. 1 for example.

As used herein, "outside primer" refers to a primer that binds non-target nucleic acid. Outside primers are designed to initiate the exonuclease activity that digests the inside primer(s) of non-target nucleic acid.

As used herein, the term "flanking" a locus of interest is meant that the sequences of the primers are such that at least a portion of the 3' region of one primer is complementary to the antisense strand of the template DNA and upstream from the locus of interest site (forward primer), and at least a portion of the 3' region of the other primer is complementary to the sense strand of the template DNA and downstream of the locus of interest (reverse primer). By a "primer pair" is intended a pair of forward and reverse primers.

Primers can be prepared by a variety of methods including but not limited to cloning of appropriate sequences and direct chemical synthesis using methods well known in the art (Narang et al., Methods Enzymol. 68:90 (1979); Brown et al., Methods Enzymol. 68:109 (1979)). Primers can also be obtained from commercial sources such as Operon Technologies, Amersham Pharmacia Biotech, Sigma, and Life Technologies. The primers can have an identical melting temperature. The lengths of the primers can be extended or shortened at the 5' end or the 3' end to produce primers with desired melting temperatures. Also, the annealing position of each primer pair can be designed such that the sequence and, length of the primer pairs yield the desired melting temperature. A simple equation for determining the melting temperature of primers smaller than 25 base pairs is the Wallace Rule (Td=2(A+T)+4(G+C)). Computer programs can also be used to design primers, including but not limited to Array Designer Software (Arrayit Inc.), Oligonucleotide Probe Sequence Design Software for Genetic Analysis (Olympus Optical Co.), NetPrimer, and DNAsis from Hitachi Software Engineering. The TM (melting or annealing temperature) of each primer can be easily calculated using methods well known in the art.

When subsequent isolation and extraction of the outside primer bound nucleic acid is preferred, the outside primers can be modified with a tag that facilitates isolation and/or extraction of the nucleic acid. In certain embodiments, the primers are modified with a tag that facilitates isolation and/or extraction of the nucleic acids. The modification can be the same for all outside primers.

The tag can be any chemical moiety including but not limited to a radioisotope, fluorescent reporter molecule, chemiluminescent reporter molecule, antibody, antibody fragment, hapten, biotin, derivative of biotin, photobiotin, iminobiotin, digoxigenin, avidin, enzyme, acridinium, sugar, enzyme, apoenzyme, homopolymeric oligonucleotide, hormone, ferromagnetic moiety, paramagnetic moiety, diamagnetic moiety, phosphorescent moiety, luminescent moiety, electrochemiluminescent moiety, chromatic moiety, moiety having a detectable electron spin resonance, electrical capacitance, dielectric constant or electrical conductivity, or combinations thereof.

In some embodiments of the invention, a primer is labeled with biotin which may bind to immobilized streptavidin (Kandpal et al., Nucleic Acids Res. 18:1789-1795 (1990); Kaneoka et al., Biotechniques 10:30-34 (1991); Green et al., Nucleic Acids Res. 18:6163-6164 (1990)). The biotin provides an affinity tag that can be used to separate the target nucleic acid from the non-target nucleic acid. Biotinylated molecules can be purified using a streptavidin coated substrate, including but not limited to Streptawell, transparent, High-Bind plates from Roche Molecular Biochemicals (catalog number 1 645 692, as listed in Roche Molecular Biochemicals, 2001 Biochemicals Catalog).

The term "functional group-coated surface" as used herein refers to a surface which is coated with moieties which bind nucleic acids. One example is a surface which is coated with moieties which each have a free functional group which is bound to the amino group of the amino silane or the solid support; as a result, the surfaces of the solid support are coated with the functional group containing moieties. In one embodiment, the functional group is a carboxylic acid. A suitable moiety with a free carboxylic acid functional group is a succinic acid moiety in which one of the carboxylic acid groups is bonded to the amine of amino silanes through an amide bond and the second carboxylic acid is unbonded, resulting in a free carboxylic acid group attached or tethered to the surface of the paramagnetic microparticle. Suitable solid phase carriers having a functional group coated surface that reversibly binds nucleic acid molecules are for example, magnetically responsive solid phase carriers having a functional group-coated surface, such as, but not limited to, silica-coated, hydroxyl-coated, amino-coated, carboxyl-coated and encapsulated carboxyl group-coated magnetic beads.

In some embodiments, phosphorus dendrimer linkers are introduced to the solid support to capture nucleic acid. For example, Archer et al. describes a magnetic bead-based method for capturing target nucleic acid with a probe (Anal Biochem. 2006 Aug. 15; 355(2):285-97). In an embodiment of the invention, the size selective methods of the present invention are combined with the improved magnetic bead-based capture methods described by Archer et al.

In some embodiments, the methods include adding a washing step or steps to remove non-nucleic acid molecules, for example salts, from the solid-support-target nucleic acid complex or surrounding solution. Non-nucleic acid molecules are then removed with an alcohol-based wash and the target nucleic acid is eluted under low- or no-salt conditions (TE buffer or water) in small volumes, ready for immediate use without further concentration. In some embodiments, extraction is improved by the introduction of a carrier such as tRNA, glycogen, polyA RNA, dextran blue, linear poly acrylamide (LPA), or any material that increases the recovery of nucleic acid.

In some embodiments, the final relative percentage of target nucleic acid to non-target nucleic acid is at least about 5-6% target DNA, about 7-8% target DNA, about 9-10% target DNA, about 11-12% target DNA, about 13-14% target DNA. about 15-16% target DNA, about 16-17% target DNA, about 17-18% target DNA, about 18-19% target DNA, about 19-20% target DNA, about 20-21% target DNA, about 21-22% target DNA, about 22-23% target DNA, about 23-24% target DNA, about 24-25% target DNA, about 25-35% target DNA, about 35-45% target DNA, about 45-55% target DNA, about 55-65% target DNA, about 65-75% target DNA, about 75-85% target DNA, about 85-90% target DNA, about 90-91% target DNA, about 91-92% target DNA, about 92-93% target DNA, about 93-94% target DNA, about 94-95% target DNA, about 95-96% target DNA, about 96-97% target DNA, about 97-98% target DNA, about 98-99% target DNA, or about 99-99.7% target DNA.

The methods provided herein may also be modified to combine steps, for example, in order to improve automation.

In another example, certain methods of the present invention may be used together with any known technique suitable for the extraction, isolation or enrichment of nucleic acids, including, but not limited to, cesium chloride gradients, gradients, sucrose gradients, glucose gradients, centrifugation protocols, boiling, Microcon 100 filter, Chemagen viral DNA/RNA 1k kit, Chemagen blood kit, Qiagen purification systems, Qiagen MinElute kits, QIA DNA blood purification kit, HiSpeed Plasmid Maxi Kit, QIAfilter plasmid kit, Promega DNA purification systems, MangeSil Paramagnetic Particle based systems, Wizard SV technology, Wizard Genomic DNA purification kit, Amersham purification systems, GFX Genomic Blood DNA purification kit, Invitrogen Life Technologies Purification Systems, CONCERT purification system, Mo Bio Laboratories purification systems, UltraClean BloodSpin Kits, and UlraClean Blood DNA Kit.

Diagnostic Applications

Circulating nucleic acids in the plasma and serum of patients can be used to diagnose or prognose certain diseases and conditions (See, Lo Y M D et al., N Eng J Med 1998; 339:1734-8; Chen X Q, et al., Nat Med 1996; 2:1033-5, Nawroz H et al., Nat Med 1996; 2:1035-7; Lo Y M D et al., Lancet 1998; 351:1329-30; Lo Y M D, et al., Clin Chem 2000; 46:319-23).

The characteristics and biological origin of circulating nucleic acids are not completely understood. However, it is likely that cell death, including apoptosis, is one major factor (Fournie et al., Gerontology 1993; 39:215-21; Fournie et al., Cancer Lett 1995; 91:221-7). Without being bound by theory, as cells undergoing apoptosis dispose nucleic acids into apoptotic bodies, it is possible that at least part of the circulating nucleic acids in the plasma or serum of human subjects is short, fragmented DNA that takes the form particle-associated nucleosomes. The present invention in part provides methods for amplifying the short, fragmented circulating nucleic acids present in biological samples, thereby enriching the short, predictive nucleic acids relative to the background genomic DNA and allowing for improved detection and sequencing.

The present invention in part provides methods of evaluating a disease condition in a patient suspected of suffering or known to suffer from the disease condition. In one embodiment of the present invention, certain methods include obtaining a biological sample from the patient suspected of suffering or known to suffer from a disease condition, selectively amplifying extracellular nucleic acid in the sample based on its size using the methods provided herein, and evaluating the disease condition by determining the amount, concentration or characteristic of enriched nucleic acid (eg, the sequence of the enriched target nucleic acid). In a related embodiment, the amount, concentration or characteristic of enriched nucleic acid may be compared to a control (e.g., nucleic acid from a healthy individual).

The phrase "evaluating a disease condition" refers to assessing the disease condition of a patient. For example, evaluating the condition of a patient can include detecting the presence or absence of the disease in the patient. Once the presence of disease in the patient is detected, evaluating the disease condition of the patient may include determining the severity of disease in the patient. It may further include using that determination to make a disease prognosis, e.g. a prognosis or treatment plan. Evaluating the condition of a patient may also include determining if a patient has a disease or has suffered from a disease condition in the past. Evaluating the disease condition in that instant might also include determining the probability of reoccurrence of the disease condition or monitoring the reoccurrence in a patient. Evaluating the disease condition might also include monitoring a patient for signs of disease. Evaluating a disease condition therefore includes detecting, diagnosing, or monitoring a disease condition in a patient as well as determining a patient prognosis or treatment plan. The method of evaluating a disease condition often aids in risk stratification.

Cancer

The methods provided herein may be used to amplify, detect or sequence oncogenic nucleic acid, which may be further used for the diagnosis or prognosis of a cancer-related disorder. In plasma from cancer patients, nucleic acids, including DNA and RNA, are known to be present (Lo K W, et al. *Clin Chem* (1999) 45, 1292-1294). These molecules are likely packaged in apoptotic bodies and, hence, rendered more stable compared to 'free RNA' (Anker P and Stroun M, *Clin Chem* (2002) 48, 1210-1211; Ng E K, et al. *Proc Natl Acad Sci USA* (2003) 100, 4748-4753). Nucleic acid derived from cancer patients display tumor-specific characteristics, including decreased strand stability, Ras and p53 mutations, mircrosatellite alterations, abnormal promoter hypermethylation, mitochondrial DNA mutations and tumor-related viral DNA (Stroun M, et al. *Oncology* (1989) 46,318-322; Chen X Q, et al. *Nat Med* (1996) 2, 1033-1035; Anker P, et al. *Cancer Metastasis Rev* (1999) 18, 65-73; Chan K C and Lo Y M,

*Histol Histopathol* (2002) 17,937-943). Tumor-specific DNA for a wide range of malignancies has been found: haematological, colorectal, pancreatic, skin, head-and-neck, lung, breast, kidney, ovarian, nasopharyngeal, liver, bladder, gastric, prostate and cervix. In aggregate, the above data show that tumor-derived DNA in plasma is ubiquitous in affected patients, and likely the result of a common biological process such as apoptosis. Investigations into the size of these plasma DNA fragments from cancer patients have revealed that the majority show lengths in multiples of nucleosomal DNA, a characteristic of apoptotic DNA fragmentation (Jahr S, et al. *Cancer Res* (2001) 61, 1659-1665).

If a cancer shows specific viral DNA sequences or tumor suppressor and/or oncogene mutant sequences, PCR-specific strategies can be developed. However, for most cancers (and most Mendelian disorders), clinical application awaits optimization of methods to isolate, quantify and characterize the tumor-specific DNA compared to the patient's normal DNA, which is also present in plasma. Therefore, understanding the molecular structure and dynamics of DNA in plasma of normal individuals is necessary to achieve further advancement in this field.

Thus, the present invention in part relates to detection of specific extracellular nucleic acid in plasma or serum fractions of human or animal blood associated with neoplastic, pre-malignant or proliferative disease. Specifically, the invention in part relates to detection of nucleic acid derived from mutant oncogenes or other tumor-associated DNA, and to those methods of detecting and monitoring extracellular mutant oncogenes or tumor-associated DNA found in the plasma or serum fraction of blood by using DNA amplification with enrichment for mutant DNA as provided herein. In certain embodiments, the invention in part relates to the detection, identification, or monitoring of the existence, progression or clinical status of benign, premalignant, or malignant neoplasms in humans or other animals that contain a mutation that is associated with the neoplasm through the size selective enrichment methods provided herein, and subsequent detection of the mutated nucleic acid of the neoplasm in the enriched DNA.

The present invention in part features methods for identifying DNA originating from a tumor in a biological sample. These methods may be used to differentiate or detect tumor-derived DNA in the form of apoptotic bodies or nucleosomes in a biological sample. In preferred embodiments, the non-cancerous DNA and tumor-derived DNA are differentiated by observing nucleic acid size differences, wherein low base pair DNA is associated with cancer.

Pathogen Detection

In some embodiments, certain methods provided herein may be used to improve pathogen detection by selectively enriching for pathogen nucleic acid, especially when pathogen nucleic acid is present in a host. Methods for rapid identification of unknown bioagents using a combination of nucleic acid amplification and determination of base composition of informative amplicons by molecular mass analysis are disclosed and claimed in published U.S. Patent applications 20030027135, 20030082539, 20030124556, 20030175696, 20030175695, 20030175697, and 20030190605 and U.S. patent application Ser. Nos. 10/326,047, 10/660,997, 10/660,122 and 10/660,996, all of which are herein incorporated by reference in their entirety.

Prenatal Diagnostics

Since 1997, it is known that free fetal DNA can be detected in the blood circulation of pregnant women. In the absence of pregnancy-associated complications, the total concentration of circulating DNA is in the range of about 10 to about 100 ng or about 1,000 to about 10,000 genome equivalents/ml plasma (Bischoff et al., Hum Reprod Update. 2005 January-February; 11(1):59-67 and references cited therein) while the concentrations of the fetal DNA fraction increases from about 20 copies/ml in the first trimester to greater than 250 copies/ml in the third trimester.

It has been demonstrated that the circulating DNA molecules are significantly larger in size in pregnant women than in non-pregnant women. Chan et al. demonstrated that the median percentages of total plasma DNA of greater than 201 base pairs were 57% and 14% for pregnant and non-pregnant women, respectively, while the median percentages of fetal-derived DNA with sizes greater than 193 base pairs and greater than 313 base pairs were only 20% and 0%, respectively (Chan et al, Clin Chem. 2004 January; 50(1):88-92). These findings were independently confirmed by Li et al. (Clin Chem. 2004 June; 50(6):1002-11; and Patent application US200516424). They showed that a greater than 5 fold relative enrichment of fetal DNA from ca. 5% to greater than 28% of total circulating plasma DNA is possible by means of size exclusion chromatography via preparative agarose gel electrophoresis and elution of the less than 300 bp size fraction. However, this method of enrichment is not practical for research or clinical use because it is difficult to automate. Also, DNA material may be lost when recovered from the relevant Agarose gel section.

Thus, the present invention in part features methods for preferentially amplifying DNA species originating from different individuals in a biological sample. These methods may be used to enrich and thereby detect fetal DNA in a maternal sample. In embodiments wherein the fetal DNA is quantified, the measured concentration may be used to predict, monitor, diagnose or prognose a pregnancy-associated disorder.

Pregnancy-Associated Disorders

The first marker that was developed for fetal DNA detection in maternal plasma was the Y chromosome (Lo et al. *Am J Hum Genet* (1998) 62:768-775). The robustness of Y chromosomal markers has been reproduced by many researchers in the field (Costa J M, et al. *Prenat Diagn* 21:1070-1074). This approach constitutes a highly accurate method for the determination of fetal gender, which is useful for the prenatal investigation of sex-linked diseases (Costa J M, Ernault P (2002) *Clin Chem* 48:679-680).

Maternal plasma DNA analysis is also useful for the non-invasive prenatal determination of fetal RhD blood group status in RhD-negative pregnant women (Lo et al. (1998) *N Engl J Med* 339:1734-1738). This approach has been shown by many groups to be accurate, and has been introduced as a routine service by the British National Blood Service since 2001 (Finning K M, et al. (2002) *Transfusion* 42:1079-1085).

More recently, maternal plasma DNA analysis has been shown to be useful for the noninvasive prenatal exclusion of fetal β-thalassemia major (Chiu R W K, et al. (2002) *Lancet* 360:998-1000). A similar approach has also been used for prenatal detection of the HbE gene (Fucharoen G, et al. (2003) *Prenat Diagn* 23:393-396).

Fetal DNA in maternal plasma can also be used for the detection of other diseases and disorders, including achondroplasia (Saito H, et al. (2000) *Lancet* 356:1170), myotonic dystrophy (Amicucci P, et al. (2000) *Clin Chem* 46:301-302), cystic fibrosis (Gonzalez-Gonzalez M C, et al. (2002) *Prenat Diagn* 22:946-948), Huntington disease (Gonzalez-Gonzalez M C, et al. (2003) *Prenat Diagn* 23:232-234), and congenital adrenal hyperplasia (Rijnders R J, et al. (2001) *Obstet Gynecol* 98:374-378). It is expected that the spectrum of such applications will increase using enrichment methods provided herein.

Thus the present invention in part features methods of detecting abnormalities in a fetus by detecting fetal DNA in a biological sample obtained from a mother. The methods according to the present invention in part provide for detecting fetal DNA in a maternal sample by preferentially amplifying fetal DNA in a background of maternal DNA based on DNA characteristics (e.g., size). See Chan et al. *Clin Chem.* 2004 January; 50(1):88-92; and Li et al. *Clin Chem.* 2004 June; 50(6):1002-11. Employing such methods, fetal DNA can be predictive of a genetic anomaly or genetic-based disease. These methods are applicable to any and all pregnancy-associated conditions for which nucleic acid changes, mutations or other characteristics (e.g., methylation state) are associated with a disease state. Exemplary diseases that may be diagnosed include, for example, preeclampsia, preterm labor, hyperemesis gravidarum, ectopic pregnancy, fetal chromosomal aneuploidy (such as trisomy 18, 21, or 13), and intrauterine growth retardation.

Certain products and processes of the present invention allow for the detection of chromosomal aberrations (e.g. aneuploidies or chromosomal aberrations associated with Down's syndrome) and hereditary Mendelian genetic disorders, including genetic markers associated therewith (e.g. single gene disorders such as cystic fibrosis or the hemoglobinopathies). Therefore, the size-based amplification, detection and sequencing of extracellular fetal DNA as described herein facilitates the non-invasive detection of fetal genetic traits, including paternally inherited alleles.

The term "pregnancy-associated disorder," as used herein, refers to any condition or disease that may affect a pregnant woman, the fetus the woman is carrying, or both the woman and the fetus. Such a condition or disease may manifest its symptoms during a limited time period, e.g., during pregnancy or delivery, or may last the entire life span of the fetus following its birth. Some examples of a pregnancy-associated disorder include ectopic pregnancy, preeclampsia, preterm labor, sex-linked disorders, and fetal chromosomal abnormalities such as trisomy 13, 18, or 21.

The term "chromosomal abnormality" refers to a deviation between the structure of the subject chromosome and a normal homologous chromosome. The term "normal" refers to the predominate karyotype or banding pattern found in healthy individuals of a particular species. A chromosomal abnormality can be numerical or structural, and includes, but is not limited to, aneuploidy, polyploidy, inversion, a trisomy, a monosomy, duplication, deletion, deletion of a part of a chromosome, addition, addition of a part of chromosome, insertion, a fragment of a chromosome, a region of a chromosome, chromosomal rearrangement, and translocation. A chromosomal abnormality can also be correlated with presence of a pathological condition or with a predisposition to develop a pathological condition.

In addition, certain products and processes of the invention may be used in conjunction with other non-invasive and invasive techniques available for detecting pregnancy-associated disorders, including ultrasonography, nuchal translucency, amniocentesis, chorionic villi sampling (CVS), fetal blood cells in maternal blood, maternal serum alpha-fetoprotein, maternal serum beta-HCG, maternal serum estriol, and other prenatal diagnostic techniques described, for example, in the following U.S. Patents and Applications: U.S. patent application Ser. No. 09/380,696, which issued Jul. 10, 2001 as U.S. Pat. No. 6,258,540; U.S. patent application Ser. No. 10/759,783, which published Oct. 14, 2004 as Application Publication No. 20040203037; U.S. patent application Ser. No. 11/378,598, which published Nov. 9, 2006 as Application Publication No. 20060252068; U.S. patent application Ser. No. 11/384,128, which published Nov. 9, 2006 as Application Publication No. 20060252071; U.S. patent application Ser. No. 10/661,165, which published Jul. 15, 2004 as Application Publication No. 20040137470; U.S. Pat. No. 6,927,028, which issued Aug. 9, 2005; U.S. patent application Ser. No. 10/346,514, which published Nov. 13, 2003 as Application Publication No. 20030211522; U.S. patent application Ser. No. 09/944,951, which issued Aug. 9, 2005 as U.S. Pat. No. 6,927,028; U.S. patent application Ser. No. 11/144,951, which published Jan. 26, 2006 as Application Publication No. 20060019278; U.S. patent application Ser. No. 10/575,119, which published Mar. 15, 2007 as Application Publication No. 20070059707; U.S. patent application Ser. No. 10/852,943, which published Feb. 17, 2005 as Application Publication No. 20050037388; and U.S. patent application Ser. No. 11/232,335, which published May 4, 2006 as Application Publication No. 20060094039.

Other Diseases

In addition to cancer and pregnancy, many other diseases, disorders and conditions (e.g., tissue or organ rejection) produce apoptotic or nucleosomal nucleic acid that may be detected by the methods provided herein. Other diseases and disorders believed to produce apoptotic nucleic acid include diabetes, heart disease, stroke, trauma, rheumatoid arthritis and lupus erythematosus (SLE) (Rumore and Steinman J Clin Invest. 1990 July; 86(1):69-74). Rumore et al. noted that DNA purified from SLE plasma formed discrete bands, corresponding to sizes of about 150-200, 400, 600, and 800 base pairs, closely resembling the characteristic 200 base pair "ladder" found with oligonucleosomal DNA.

The present invention therefore in part provides methods of evaluating the disease condition of a patient suspected of having suffered from a trauma or known to have suffered from a trauma. The methods include obtaining a sample of plasma or serum from the patient suspected of having suffered from a trauma or known to have had suffered from a trauma, and detecting the quantity or concentration of mitochondrial nucleic acid in the sample.

Each document cited throughout the specification, and each document cited therein, is hereby expressly incorporated herein by reference in its entirety.

EXAMPLES

The examples hereafter illustrate but do not limit the invention.

Example 1

Preferential Amplification of Short-Stranded DNA Using Universal Size Specific PCR The below example provides a process, using a method provided herein, to preferentially amplify, and thereby enrich, target DNA based on its size using inside and outside primers in combination with universal PCR. A schematic showing the general features of this method is provided in FIG. 1. The primer sequences, PCR sequences, universal primers, long and short DNA sequences, and genomic sequences referred to in this Example are provided in FIG. 4.

1. DNA Dilutions

Figure 2B:
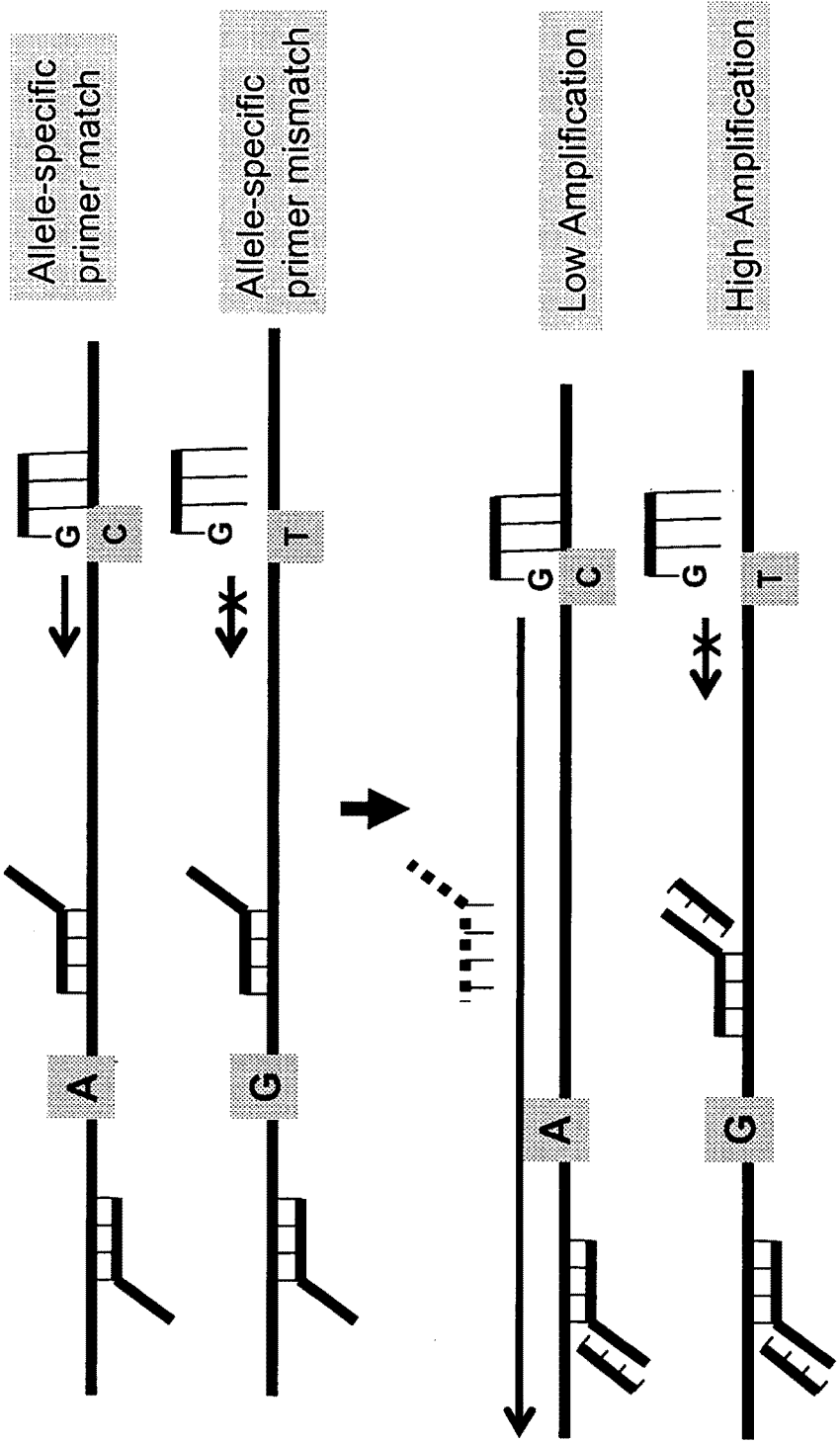

First, 800 bp and 200 bp DNA fragments were generated by PCR. Both the long fragments (actual length=783 bp) and short fragments (actual length=169 bp) included a single nucleotide polymorphism (SNP) rs6687785—an NT polymorphism. Two different samples (Sample 1 and Sample 2) of known sequence at SNP rs6687785 were used to generate the long and short DNA fragments, thereby ensuring the long DNA fragment was homozygote for the A allele, and the short DNA fragment was homozygote for the T allele. See FIG. 2.

Next, long and short DNA fragments were diluted according to Table 1 to ensure equal starting concentrations of the 800 bp and 200 bp products.

TABLE 1

Equal DNA Starting Concentration

| Large DNA number | PCR product (ul) | H2O (ul) | Dilution factors | Small DNA number | PCR product (ul) | H2O (ul) | Dilution factors |
|---|---|---|---|---|---|---|---|
| Sample 1 | 10 | 990 | X100 | Sample 1 | 6 | 9998 | X5000 |
| Sample 2 | 10 | 990 | X100 | Sample 2 | 10 | 9998 | X5000 |

Next, the long and short DNA mixes from Table 1 were combined at different ratios as summarized below in Table 2:

TABLE 2

Test Ratios of Long-to-Short DNA

| Ratio | Long DNA (ul) | Short DNA (ul) | Sub Total | H20 | Total (ul) |
|---|---|---|---|---|---|
| 1:1 | 25 | 25 | 50 | 450 | 500 |
| 5:1 | 40 | 10 | 50 | 450 | 500 |
| 10:1 | 45 | 5 | 50 | 450 | 500 |
| 50:1 | 98 | 2 | 100 | 900 | 1000 |
| 100:1 | 198 | 2 | 200 | 1800 | 2000 |
| 200:1 | 398 | 2 | 400 | 3600 | 4000 |
| 0:1 | 0 | 50 | 50 | 450 | 500 |
| 1:0 | 50 | 0 | 50 | 450 | 500 |

2. Primer Mix Preparation for Standard and USS PCR and Preferential Amplification Next, 15 μl of Standard and USS primer mix were prepared, which were added to the PCR reactions. The standard PCR reaction comprised inside primers, whereas the USS PCR comprised a mixture of inside primers, outside primers, and universal primers. The concentrations of all the primers in both mixes are provided in Table 3. All of the primer sequences are provided in FIG. 4.

TABLE 3

USS PCR Primer Mix

| 0.75 uM | Standard | UPCR1 |
|---|---|---|
| Inside Primer Mix | 15 | 2 |
| Outside Primer Mix | 0 | 4 |
| Universal Primer | 0 | 9 |

The primer mix for both standard PCR and USS PCR was added to the different ratios of long and short DNA, and a standard amplification was run as described below in step 3.

3. Quantitative Analysis of Long and Short Fragment DNA

First, the target DNA was subjected to PCR amplification using the reagents provided in Table 4. The MassARRAY® primers are provided in FIG. 4. In this Example, the MassARRAY® primers are the same as the inside primers.

TABLE 4

PCR Reagents

| Reagents | Conc. | 1 Well (ul) |
|---|---|---|
| H$_2$O |  | 1.275 |
| PCR buffer | 10X | 0.625 |
| MgCl$_2$ | 25 mM | 0.5 |
| dNTPmix | 25 mM | 0.1 |
| F/R primer | 1.25 | 0.4 |
| Enzyme Taq | 5u | 0.1 |
| Total Volume | ul | 3.0 |

PCR cycling was performed for 45 cycles, where each cycle is 94° C. for 15 minutes, 94° C. for 20 seconds, 56° C. for 30 seconds, 72° C. for 1 minute, 72° C. for 3 minutes. Then the products were maintained at 4° C. thereafter.

PCR amplification was followed by SAP cleanup using the reagents in Table 5.

TABLE 5

SAP Reagents

| SAP Step | microliter |
|---|---|
| H$_2$O | 1.33 |
| 10XSAP Buffer | 0.17 |
| SAP Enzyme | 0.5 |
| Total | 2 |

Two microliters of the SAP mix were added to each 5 microliter PCR reaction; then maintained at the following temperatures: 37° C. for 20 minutes, 85° C. for 5 minutes and 4° C. thereafter.

Next, a MassEXTEND® reaction was performed using the reagents provided in Table 6 to detect the different alleles in the standard and USS-PCR products.

TABLE 6

MassEXTEND ® Reagents

| Reagents | Conc. | 1 Well (microliter) |
|---|---|---|
| H$_2$O |  | 0.4 |
| EXT buffer | 10X | 0.2 |
| MgCl$_2$ | 100 mM | 0.0 |
| Term. mix | iPLEX | 0.2 |
| E Oligo mix | 2 Tiers | 1 |
| Enzyme | TP | 0.2 |
| Total Volume | microliter | 2.0 |

For iPLEX extension, 200 short cycles were carried out, where each cycle includes 94° C. for 30 seconds, 94° C. for 5 seconds, 52° C. for 5 seconds, 80° C. for 5 seconds and 72° C. for 3 minutes, and then the products were maintained at 4° C. thereafter.

The samples were deslated with 6 mg of resin, dispensed to SpectroChip® Bioarrays and analyzed on a Sequenom® MALDI-TOF MS system. The resulting spectrographs are provided in FIGS. 3A and 3B. They show the relative enrichment of the target nucleic acid after preferential amplification of the target nucleic acid.

Preferential Amplification of Short DNA (120 Base Pair) in a Genomic DNA Sample

A method of the invention can be used to preferentially amplify, and thereby enrich, short target DNA from a sample of genomic DNA. In the following example, inside and outside primers were used in combination with universal PCR primers to amplify a 120 base pair fragment of genomic DNA. The outside primers (for amplifying a 530 base pair amplicon), the inside primers (for amplifying the 120 base pair amplicon), and the universal primer sequence (for preferentially amplifying the 120 base pair amplicon) are disclosed in Table 7 below.

TABLE 7

| Primer | Sequence | SEQ ID NO: |
|---|---|---|
| Outside Fwd Primer (OFP) | ACGTTGGATGCTGACTTTTTAATGATTGCCATTC | 1 |
| Outside Rev Primer (ORP) | ACGTTGGATGCCTAAAACCATAAAAACCCTAGAAG | 2 |
| Inside Fwd Primer (IFP) | TCGACCCGGAGCACGTTGGATGATATTAGCCCTTTGTCAGATG | 3 |
| Inside Rev Primer (IRP) | TCGACCCGGAGCACGTTGGATCTATCATCAGAGTGAACAGGC | 4 |
| Universal Primer (UP) | AGCGGATAATCGACCCGGAGCACGTTGGAT | 5 |

Figure 5:
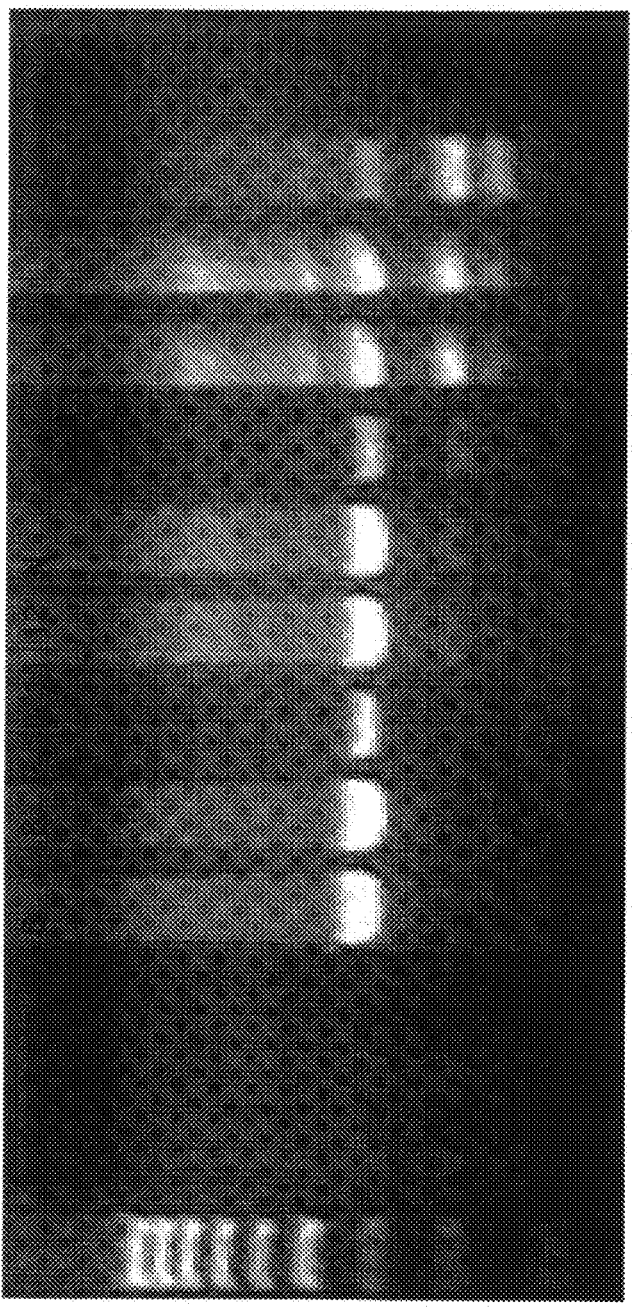
FIG. 5 shows amplification products resulting from the PCR cocktails provided in Table 8.

The gel picture provided in FIG. 5 shows the amplification products resulting from the PCR cocktails provided in Table 8. For example, lanes 1-3 show the amplification products resulting from the PCR cocktail containing 0.05 inside primers and no universal primer or outside primers. This approach resulted in only minimal amplification that is hard to detect in the gel due to the small amplicon size. Lanes 4-6 show the amplification products resulting from the PCR cocktail containing 0.1 outside primers but no inside primers or universal primer. This approach resulted in the amplification of the 530 bp fragment, but not the 120 bp fragment. Lanes 7-9 show the amplification products resulting from the PCR cocktail containing the outside and inside primers, but no universal primer. This approach results in amplification of the long amplicon but only slight amplification of the short amplicon. Lanes 10-12 show the amplification products resulting from the PCR cocktail containing the outside, inside and universal primers which results in a clear increase in the short amplicon. All units in the IFP, IRP, UP, OFP and ORP columns of Table 8 are micromolar.

TABLE 8

| Gel Lane | IFP | IRP | UP | OFP | ORP |
|---|---|---|---|---|---|
| 1-3 | 0.05 | 0.05 | | | |
| 4-6 | | | | 0.1 | 0.1 |
| 7-9 | 0.05 | 0.05 | | 0.1 | 0.1 |
| 10-12 | 0.05 | 0.05 | 1 | 0.1 | 0.1 |
| Negative Control | 0 | 0 | 0 | 0 | 0 |

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents. Singular forms "a", "an", and "the" include plural reference unless the context clearly dictates otherwise. Thus, for example, reference to "a subset" includes a plurality of such subsets, reference to "a nucleic acid" includes one or more nucleic acids and equivalents thereof known to those skilled in the art, and so forth. The term "or" is not meant to be exclusive to one or the terms it designates. For example, as it is used in a phrase of the structure "A or B" may denote A alone, B alone, or both A and B.

Unless defined otherwise, all technical and scientific terms used herein have the same meanings as commonly understood by one of ordinary skill in the art to which this invention belongs. Although any methods and systems similar or equivalent to those described herein can be used in the practice or testing of the present invention, the methods, devices, and materials are now described. All publications mentioned herein are incorporated herein by reference for the purpose of describing and disclosing the processes, systems, and methodologies that are reported in the publications which might be used in connection with the invention. Nothing herein is to be construed as an admission that the invention is not entitled to antedate such disclosure by virtue of prior invention.

What is claimed is:

1. A method of enriching for a target nucleic acid in a sample containing a mixture of target and non-target nucleic acid, comprising the steps of:
   a) introducing to the sample a pair of forward and reverse inside primers that bind target and non-target nucleic acid, wherein:
      (i) the target nucleic acid is a low copy number, relatively short nucleic acid of at least about 75 base pairs, but less than about 1200 base pairs and the non-target nucleic acid is an abundant copy number nucleic acid that is longer than the target nucleic acid, and
      (ii) the inside primers comprise a common, universal domain and a sequence-specific domain complementary to both the target and non-target nucleic acids;
   b) introducing to the sample an outside non-target binding primer at a concentration two times or more greater than the inside primer, wherein:
      (i) the inside primers and outside primer are introduced to the sample at a concentration greater than the concentration of non-target nucleic acid, and
      (ii) the outside non-target binding primer anneals upstream or downstream of the inside primer and is complementary to non-target nucleic acid, but not target nucleic acid;
   c) introducing to the sample a universal primer capable of binding to the universal domain of the inside primers, wherein the universal primer is introduced at a concentration greater than the outside primer;
   d) performing an amplification reaction using a polymerase having exonuclease activity, wherein:
      (i) amplification of the non-target nucleic acid is initiated by the outside primer bound to one strand of the non-target nucleic acid, whereby the exonuclease activity digests the inside primer bound to the same strand of the non-target nucleic acid;
      (ii) the outside primer does not bind to the target nucleic acid and amplification of the target nucleic acid is not initiated by the outside primer; and
      (iii) amplification of the target nucleic acid is initiated by the inside primers, whereby the target nucleic acid is preferentially amplified relative to the non-target nucleic acid and whereby the target nucleic acid in the sample is enriched.

2. The method of claim 1, wherein a pair of forward and reverse outside primers are introduced, whereby both inside primers bound to the non-target nucleic acid are digested during amplification.

3. The method of claim 1, wherein the universal primer is introduced at a concentration about ten times greater than the inside primers, and the outside primer is introduced at a concentration about two times greater than the inside primer.

4. The method of claim 1, wherein multiple target nucleic acids are detected in a single, multiplexed reaction.

5. The method of claim 1, wherein the outside, non-target binding primers anneal to the non-target nucleic acid at least about 300 base pairs upstream of the inside primer.

6. The method of claim 1, wherein the inside primers contain a label.

7. The method of claim 1, wherein the inside primers are modified to facilitate their capture.

8. The method of claim 7, wherein the modifications are selected from the group consisting of capture mechanisms, compomers, tags, linkers and adapter molecules.

9. The method of claim 1, wherein the sample comprises cell-free nucleic acid.

10. The method of claim 1, wherein the target nucleic acid is an apoptotic product.

11. The method of claim 1, wherein the target nucleic acid is of fetal origin.

12. The method of claim 1, wherein the target nucleic acid comprises a locus of interest.

13. The method of claim 12, which further comprises determining the identity of at least one allele within the locus of interest.

14. The method of claim 12, wherein the inside primers are less than about 200 base pairs apart.

15. The method of claim 13, wherein the at least one allele falls between the inside primers.

16. The method of claim 13, wherein the outside primer is greater than about 250 base pairs 5' upstream of the at least one allele.

17. The method of claim 1, wherein the non-target nucleic acid is of maternal origin.

18. The method of claim 1, wherein the sample is from a human.

19. The method of claim 1, wherein the sample is from a pregnant human.

20. The method of claim 19, wherein the sample is collected after the fifth week of gestation.

21. The method of claim 1, wherein the sample is selected from the group consisting of whole blood, serum, plasma, umbilical cord blood, chorionic villi, amniotic fluid, cerbrospinal fluid, spinal fluid, lavage fluid, biopsy sample, urine, feces, sputum, saliva, nasal mucous, prostate fluid, semen, lymphatic fluid, bile, tears, sweat, breast milk, breast fluid, embryonic cells and fetal cells.

22. The method of claim 1, wherein the sample is plasma.

23. The method of claim 1, wherein the sample is a previously isolated sample of nucleic acids.

24. The method of claim 1, wherein prior to (a), the sample is lysed in the presence of a lysis buffer, chaotropic substance and proteinase or protease, or any combination thereof.

25. A method for detecting a target nucleic acid, wherein the method of claim 1 is performed prior to, subsequent to, or simultaneously with another method for selectively detecting nucleic acid.

26. The method of claim 25, wherein the other method is selected from the group consisting of electrophoresis, liquid chromatography, size exclusion, microdialysis, electrodialysis, centrifugal membrane exclusion, organic or inorganic extraction, affinity chromatography, PCR, genome-wide PCR, sequence-specific PCR, methylation-specific PCR, restriction endonuclease enhanced polymorphic sequence detection, introducing a silica membrane or molecular sieve, and fragment selective amplification, or combinations thereof.

27. The method of claim 1, wherein the final relative percentage of target nucleic acid to non-target nucleic acid is at least about 25%.

28. The method of claim 1, further comprising quantifying the amplification products.

29. The method of claim 1, wherein the size of the target nucleic acid is about 500 base pairs or less and the size of the non-target nucleic acid is greater than about 500 base pairs.

30. The method of claim 29, wherein the target nucleic acid is of fetal origin.

31. The method of claim 29, wherein the non-target nucleic acid is of maternal origin.

32. The method of claim 30, wherein the non-target nucleic acid is of maternal origin.

33. The method of claim 30, wherein the sample is from a pregnant human.

34. The method of claim 1, further comprising detecting the preferentially amplified target nucleic acid.

* * * * *